(12) United States Patent
Klauber et al.

(10) Patent No.: US 10,975,036 B2
(45) Date of Patent: Apr. 13, 2021

(54) CATALYTIC HYDROGENATION PROCESS FOR PREPARING PYRAZOLES

(71) Applicant: BASF SE, Ludwigshafen (DE)

(72) Inventors: Eric George Klauber, Huntsville, AL (US); Michael Rack, Ludwigshafen (DE); Sebastian Soergel, Limburgerhof (DE); Birgit Gockel, Ludwigshafen (DE); Roland Goetz, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/074,537

(22) PCT Filed: Jan. 25, 2017

(86) PCT No.: PCT/EP2017/051524
§ 371 (c)(1),
(2) Date: Aug. 1, 2018

(87) PCT Pub. No.: WO2017/133942
PCT Pub. Date: Aug. 10, 2017

(65) Prior Publication Data
US 2019/0055200 A1 Feb. 21, 2019

(30) Foreign Application Priority Data

Feb. 2, 2016 (EP) .................................. 16153833

(51) Int. Cl.
| | | |
|---|---|---|
| *C07D 231/14* | (2006.01) | |
| *C07C 251/76* | (2006.01) | |
| *C07D 401/12* | (2006.01) | |
| *B01J 21/18* | (2006.01) | |
| *B01J 23/42* | (2006.01) | |
| *C07C 249/16* | (2006.01) | |
| *C07D 403/12* | (2006.01) | |

(52) U.S. Cl.
CPC ............ *C07D 231/14* (2013.01); *B01J 21/18* (2013.01); *B01J 23/42* (2013.01); *C07C 249/16* (2013.01); *C07D 401/12* (2013.01); *C07D 403/12* (2013.01)

(58) Field of Classification Search
CPC .................. C07C 251/76; C07D 231/14
See application file for complete search history.

(56) References Cited

U.S. PATENT DOCUMENTS

| 8,987,461 B2 | 3/2015 | Nie et al. | |
| 10,414,733 B2 * | 9/2019 | Gockel | C07D 231/14 |
| 2010/0305124 A1 | 12/2010 | Fusslein | |
| 2013/0324547 A1 | 12/2013 | Boivin | |

FOREIGN PATENT DOCUMENTS

| EP | 2671873 A1 | 12/2013 |
| JP | 2007326784 A2 | 12/2007 |
| WO | 09027393 A2 | 3/2009 |
| WO | 09068652 A1 | 6/2009 |
| WO | WO10034737 A1 | 4/2010 |
| WO | WO10034738 A2 | 4/2010 |
| WO | WO10112177 A1 | 10/2010 |
| WO | WO10142628 A1 | 12/2010 |
| WO | WO12019015 A2 | 2/2012 |
| WO | 12142217 A1 | 10/2012 |
| WO | 12143317 A1 | 10/2012 |
| WO | 13189801 A1 | 12/2013 |
| WO | WO16016369 A1 | 2/2016 |
| WO | WO16180833 A1 | 11/2016 |

OTHER PUBLICATIONS

A. Alemagna et al., "Arylazomethylenetriphenylphosphoranes: intra molecular reactions with aldonitronyl substituents in the ortho position with respect to the azophosphorane group", Tetrahedron, vol. 41, No. 12, Jan. 1, 1985, pp. 2503-2511.

S.I. Yakimovich et al., "Reactions of 3-ethoxymethylidenipentane-2, 4-dione and ethyl 2-ethoxymethylidene-3, oxobutanoate with benzohydrazide," Russian Journal of Organic Chemistry, vol. 44, No. 4, Apr. 1, 2008, pp. 621-623.

N.A. Konyukhova et al., "Chemistry of Heterocyclic Compounds," vol. 37, No. 6, Jan. 1, 2001, pp. 779-780.

Lipunova G N et al., "Fluorine-Containing Heterocycles: VIII. Transformations of 2-Polyfluorobenzoylacrylates Having a Thiosemicarbazide Fragment," Russian Journal of Organic Chemistry, Consultants Bureau, US, vol. 38, No. 12, Dec. 1, 2002, pp. 1851-1856.

(Continued)

*Primary Examiner* — Susanna Moore

(74) *Attorney, Agent, or Firm* — Marshall, Gerstein & Borun LLP

(57) ABSTRACT

The present invention relates to a catalytic process for preparing pyrazoles of formula V comprising the step of cyclizing hydrazone substituted α,β-unsaturated carbonyl compounds by reacting them with hydrogen in a reaction mixture comprising as components (a) a hydrogenation catalyst, (b) an acid selected from Brønsted acids, ammonium salts of Brønsted acids, and Lewis acids, (c) a protic solvent, and optionally (d) an aprotic solvent.

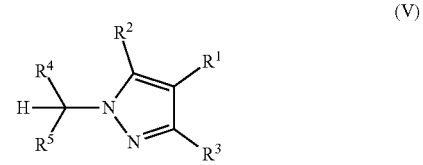

(V)

23 Claims, 1 Drawing Sheet

(56) References Cited

OTHER PUBLICATIONS

Kralj D et al., "3-(Dimethylamino) Propenoate-Based Regioselective Synthesis of 1, 4-Dusibstituted 5-Hydroxy-1-Hpyrazoles," Heterocycles: An International Journal For Review and Communications in Heterocyclic Chemistry, Japan Institute of Heterocyclic Chemistry, JP, vol. 68, No. 5, Mar. 31, 2006, pp. 897-914.
Holschbach, MH et al., "Synthesis of 2-benzyl-2H-pyrazole-3, 4-diamine dihydrochloride," Tetrahedron Letters, Pergamon, GB, vol. 44, No. 1, Jan. 1, 2003, pp. 41-43.
Weigert et al.,"Hexafluoracetone hydrazone chemistry," Journal of Flourine Chemistry, Elsevier NL, vol. 1, No. 4, Apr. 1, 1972, pp. 445-462.
Altenbach, et al., "Synthesis, Potency, and In Vivo Profiles of Quinoline Containing Histamine H3 Receptor Inverse Agonists", Journal of Medicinal Chemistry, vol. 50, Issue 22, 2007, pp. 5439-5448.
European Search Report for EP Patent Application No. 16153833.5, dated Mar. 30, 2016, 4 pages.
International Search Report for PCT Patent Application No. PCT/EP2017/051524, dated Feb. 27, 2017, 4 pages.
Yakimovich, et al., "Reactions of 3-ethoxymethylidenepentane-2,4-dione and ethyl 2-ethoxymethylidene-3-oxobutanoate with benzohydrazide", Russian Journal of Organic Chemistry, vol. 44, Issue 4, Apr. 2008, pp. 621-623.
International Preliminary Report on Patentability, issued in PCT/EP2017/051524, dated Mar. 8, 2018.

\* cited by examiner

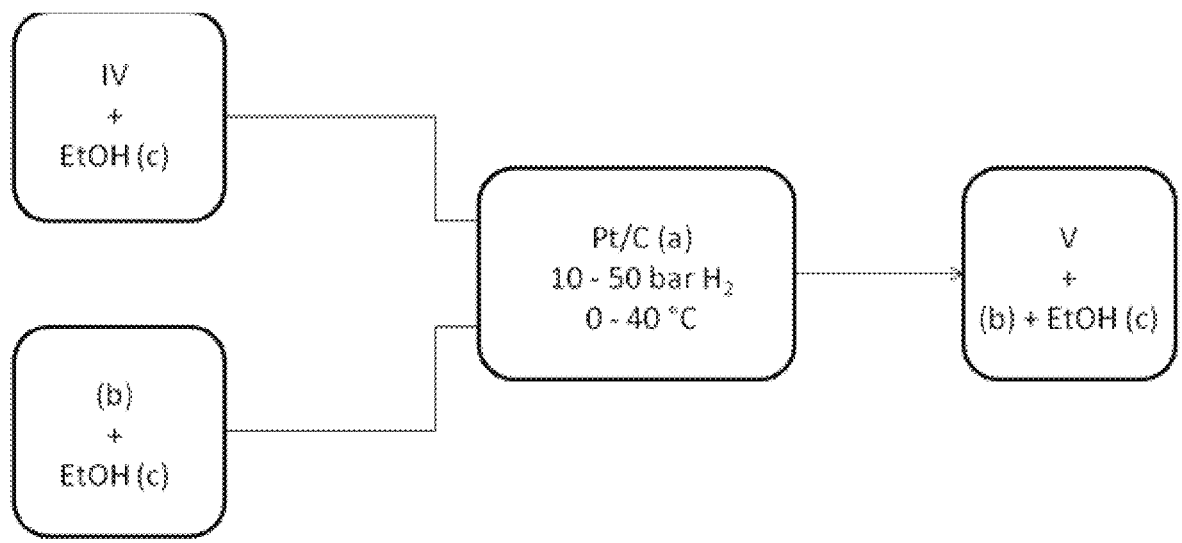

CATALYTIC HYDROGENATION PROCESS FOR PREPARING PYRAZOLES

This application is a National Stage application of International Application No. PCT/EP2017/051524, filed Jan. 25, 2017. This application also claims priority under 35 U.S.C. § 119 to European Patent Application No. 16153833.5, filed Feb. 2, 2016.

The present invention relates to a catalytic process for preparing pyrazoles comprising the step of cyclizing hydrazone substituted α,β-unsaturated carbonyl compounds by reacting them with hydrogen in a reaction mixture comprising as components (a) a hydrogenation catalyst, (b) an acid selected from Brønsted acids, ammonium salts of Brønsted acids, and Lewis acids, (c) a protic solvent, and optionally (d) an aprotic solvent.

In this connection, the present invention also covers the preparation of hydrazone substituted α,β-unsaturated carbonyl compounds. The preparation of pyrazoles may thus be performed according to the following reaction sequence:

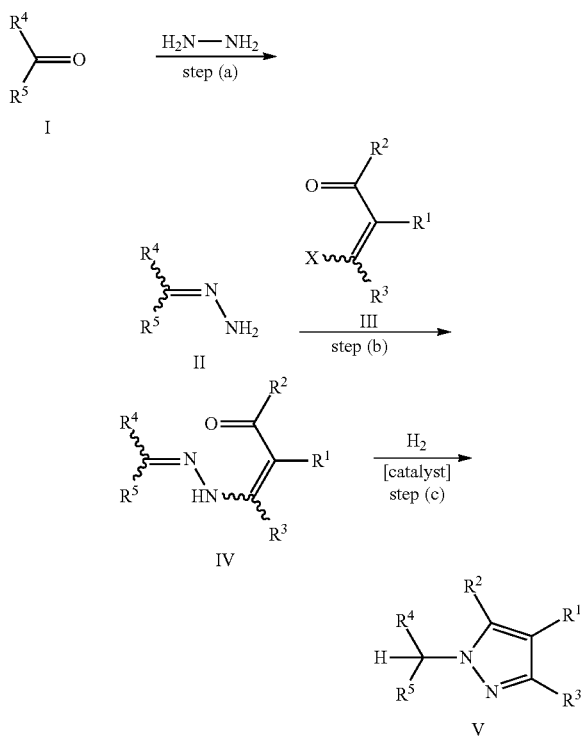

The present invention particularly relates to the final step of cyclizing the hydrazone substituted α,β-unsaturated carbonyl compounds of formula IV (also referred to as pyrazole precursors IV) under the above mentioned reaction conditions to provide the desired pyrazole compounds of formula V.

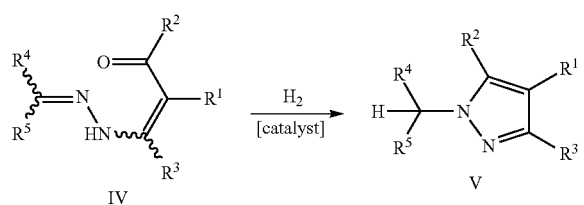

Pyrazole compounds, in particular 4-pyrazole carboxylic acid derivatives, such as esters, nitriles, acids and activated acid derivatives, are versatile intermediate compounds for the preparation of pyrazole derived fine chemicals, such as compounds in the pharmaceutical or agrochemical field. In particular the compounds are versatile intermediate compounds for the preparation of pyrazole derived pesticides, such as 4-pyrazole N-(het)arylamide compounds, which are known to be particularly useful for combating invertebrate pests (see WO 2009/027393, WO 2010/034737, WO 2010/034738, and WO 2010/112177). Of particular interest are pyrazole compounds and 4-pyrazole carboxylic acid derivatives, which are substituted at one nitrogen atom and optionally also substituted in the 3- and/or 5-position because also the pyrazole derived pesticides including the above mentioned 4-pyrazole amide compounds often comprise pyrazole moieties, which are substituted accordingly.

It is noted that the numbering of the atoms of an N-substituted pyrazole compound is usually as follows.

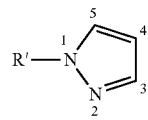

The positions of the substituents are indicated by the same numbers. The substituent at the nitrogen atom is typically referred to as the N-substituent rather than as substituent in the 1-position, although this is also suitable. The 2-position, i.e. the second nitrogen atom of the N-substituted pyrazole compounds, is typically unsubstituted. In contrast, the 3-, 4- and 5-positions may each be substituted.

In view of the above, there is a need for processes for the preparation of N-substituted pyrazole compounds. A particular problem accompanying the preparation of N-substituted pyrazole compounds is the regioselectivity, if substituents are present in the 3- and/or 5-position of the pyrazole ring, in particular, if a substituent is present in the 3-position, but not in the 5-position, if a substituent is present in the 5-position, but not in the 3-position, or if different substituents are present in the 3- and 5-position. Accordingly, there is a particular need for a process for regioselectively preparing N-substituted pyrazole compounds, which have a substituent either in the 3- or in the 5-position or different substituents in the 3- and 5-position of the pyrazole ring. In view of the preparation of 4-pyrazole N-(het)arylamide compounds as pesticides, such a process should particularly be suitable for regioselectively obtaining N-substituted 4-pyrazole carboxylic acid derivatives, which have a substituent either in the 3- or in the 5-position or different substituents in the 3- and 5-position of the pyrazole ring.

There are principally two processes known for the preparation of N-substituted 4-pyrazole carboxylic acid derivatives, which are 3- and/or 5-substituted.

Firstly, such N-substituted 4-pyrazole carboxylic acid derivatives can be prepared by reacting an α,β-unsaturated carbonyl compound, e.g. an α,β-unsaturated ketone, which contains a leaving group in the 3-position, with a hydrazine derivative, which has a substituent at one of the two nitrogen atoms. In view of the fact that the substituted hydrazine derivative comprises two amino groups, which are often very similar in terms of their nucleophilic reactivity, two regioisomers of the desired N-substituted pyrazole compound are usually obtained because either the substituted nitrogen atom or the unsubstituted nitrogen atom of the hydrazine derivative may react. Reactions, wherein the substituted hydrazine derivatives are used in the form of salts, have already been described, e.g., in JP 2007/326784, WO 2010/142628, and WO 2012/019015, and reactions, wherein mono-protected substituted hydrazine derivatives are used, have been described in WO 2012/019015. However, the regioselectivity problem in terms of the 3-/5-substitution pattern of the resulting N-substituted 4-pyrazole carboxylic acid derivatives could not be solved.

Secondly, N-substituted 4-pyrazole carboxylic acid derivatives, which are 3- and/or 5-substituted, can be prepared by reacting an α,β-unsaturated carbonyl compound, e.g. an α,β-unsaturated ketone, which contains a leaving group in the β-position, with hydrazine and then N-alkylating the resulting pyrazole derivative. Due to the tautomerism of the pyrazole compound, which is obtained as an intermediate, two regioisomers of the desired N-substituted pyrazole compound are usually obtained upon alkylation. Such reaction sequences have, e.g., been described in Heterocycles 2000, 2775, Liebigs Analen der Chemie 1985, 794, or Journal of Heterocyclic Chemistry 1985, 1109.

A process for regioselectively preparing certain N-substituted 4-pyrazole carboxylic acid derivatives, which are 3-substituted, but not 5-substituted, is known from EP 2671873. Said process is performed by comprising cyclizing a hydrazone substituted α,β-unsaturated carbonyl compound under UV light irradiation.

Although the process regioselectively provides certain N-substituted 4-pyrazole carboxylic acid derivatives, which are only 3-substituted, the process is disadvantageous in that the process works only for certain N- and 3-substituents, and the imino group of the hydrazone is split off by cyclisation, so that the process produces equimolar waste material.

A process for regioselectively preparing N-substituted 4-pyrazole carboxylic acid derivatives, which are 3-substituted or 3- and 5-substituted with different substituents, was published by Glorius et al. in Angew. Chem. Int. Ed. 2010, 7790, and Green Chem. 2012, 14, 2193. Said process is performed by reacting an enamine compound with an excess of a suitable nitrile compound in the presence of stoichiometric or catalytic amounts of copper.

Although the process regioselectively provides N-substituted 4-pyrazole carboxylic acid derivatives, which are 3-substituted or 3- and 5-substituted with different substituents, the process is disadvantageous in that an excess of at least three equivalents of the nitrile compound has to be used, so that the process is not economical. Furthermore, the process has not been described for HCN as nitrile compound, most likely for the reason that HCN would polymerize under the reaction conditions, so that a cyclization reaction with the enamine compound according to the above reaction scheme would not take place. As a consequence, N-substituted 4-pyrazole carboxylic acid derivatives, which are 5-substituted, but not 3-substituted, can obviously not be obtained according to the process described by Glorius et al.

Against this background, an improved process for regioselectively preparing N-substituted pyrazole compounds was described in PCT/EP2015/067507. According to this process, pyrazoles may be prepared by cyclizing hydrazone substituted α,β-unsaturated carbonyl compounds by reacting them with a certain reagent, for example a reducing agent. According to the examples of PCT/EP2015/067507, said reagent is preferably sodium cyanoborohydride, which is reacted with the hydrazone substituted α,β-unsaturated carbonyl compounds in the presence of acetic acid to provide the desired pyrazole compounds.

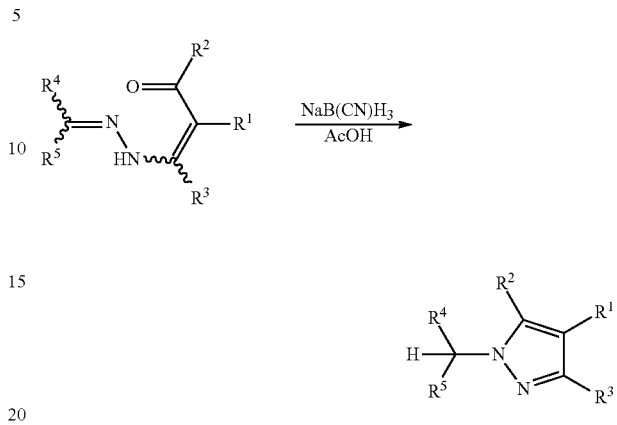

However, this process has the disadvantage that the reducing agent has to be used at least in stoichiometric amounts. Furthermore, the exemplified reducing agent sodium cyanoborohydride is highly toxic and expensive, so that it is not well-suited for large scale application. Another disadvantage in this connection is the tedious work-up of sodium cyanoborohydride, especially on production scale.

It is therefore an object of the present invention to provide an improved process for preparing N-substituted pyrazole compounds. Depending on the substitution pattern of the pyrazole compounds, it is also desired to provide a process, which is regioselective. Furthermore, it is desired that the process is cost-effective and suitable for large scale application. In this connection, it is also desired to reduce side reactions, so that high yields of the desired pyrazole compounds can be obtained.

It is another object of the present invention to provide a process, which allows for the preparation of N-substituted pyrazole compounds from readily and cheaply available starting materials. In particular, it is desired that the process can be performed as a one-pot procedure, wherein the pyrazole precursor is prepared and then converted into the pyrazole compound without previous purification. In this connection, it is also desired to provide a composition comprising the pyrazole precursor, which can be used as a starting material for the preparation of the pyrazole compound.

The objects underlying the invention are achieved by the process and the composition described in detail in the claims and hereinafter.

In particular, the present invention relates to a process for preparing a pyrazole compound of formula V, or a salt, stereoisomer, tautomer or N-oxide thereof

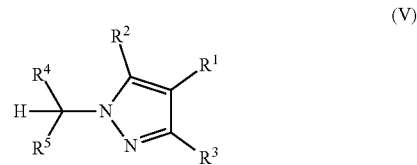

(V)

comprising the step of cyclizing a hydrazone substituted α,β-unsaturated carbonyl compound of formula IV

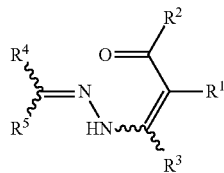
(IV)

by reacting it with hydrogen,
wherein the compound of formula IV is provided in a reaction mixture comprising as components:
(a) a hydrogenation catalyst;
(b) an acid selected from Brønsted acids, ammonium salts of Brønsted acids, and Lewis acids;
(c) a protic solvent; and optionally
(d) an aprotic solvent;
and wherein
$R^1$ is selected from H, halogen, CN, $NO_2$, $C_1$-$C_{10}$-alkyl, $C_2$-$C_{10}$-alkenyl, $C_2$-$C_{10}$-alkynyl, wherein the aliphatic groups are unsubstituted, partially or fully halogenated, or substituted by one or more identical or different substituents $R^x$;
$OR^a$, $SR^a$, $C(Y)OR^c$, $S(O)_mR^d$, $S(O)_mY^1R^d$, $NR^eR^f$, $C(Y)NR^gR^h$, heterocyclyl, hetaryl, $C_3$-$C_{10}$-cycloalkyl, $C_3$-$C_{10}$-cycloalkenyl, and aryl, wherein the cyclic moieties are unsubstituted or substituted by one or more identical or different substituents selected from the radicals $R^y$ and $R^x$;
$R^2$ is selected from H, $C_1$-$C_{10}$-alkyl, $C_2$-$C_{10}$-alkenyl, $C_2$-$C_{10}$-alkynyl, wherein the aliphatic groups are unsubstituted, partially or fully halogenated, or substituted by one or more identical or different substituents $R^x$;
$C(Y)OR^c$, $C(Y)NR^gR^h$, heterocyclyl, hetaryl, $C_3$-$C_{10}$-cycloalkyl, $C_3$-$C_{10}$-cycloalkenyl and aryl, wherein the cyclic moieties are unsubstituted or substituted by one or more identical or different substituents selected from the radicals $R^y$ and $R^x$; and
$R^3$ is selected from H, halogen, CN, $NO_2$, $C_1$-$C_{10}$-alkyl, $C_2$-$C_{10}$-alkenyl, $C_2$-$C_{10}$-alkynyl, wherein the aliphatic groups are unsubstituted, partially or fully halogenated, or substituted by one or more identical or different substituents $R^x$;
$OR^a$, $SR^a$, $C(Y)OR^c$, $S(O)_mR^d$, $S(O)_mY^1R^d$, $NR^eR^f$, $C(Y)NR^gR^h$, heterocyclyl, hetaryl, $C_3$-$C_{10}$-cycloalkyl, $C_3$-$C_{10}$-cycloalkenyl, and aryl, wherein the cyclic moieties are unsubstituted or substituted by one or more identical or different substituents selected from the radicals $R^y$ and $R^x$;
and wherein
$R^4$ and $R^5$ are independently of each other selected from H, $NO_2$, $C_1$-$C_{10}$-alkyl, $C_2$-$C_{10}$-alkenyl, $C_2$-$C_{10}$-alkynyl, wherein the aliphatic groups are unsubstituted, partially or fully halogenated, or substituted by one or more identical or different substituents $R^x$;
$C_1$-$C_{10}$-haloalkyl, $C_1$-$C_4$-alkoxy-$C_1$-$C_{10}$-alkyl, wherein the groups are unsubstituted, or substituted by one or more identical or different substituents $R^y$;
$C(Y)OR^c$, $C(Y)NR^gR^h$, $C(Y)NR^iNR^eR^f$, $C_1$-$C_5$-alkylen-$OR^a$, $C_1$-$C_5$-alkylen-CN, $C_1$-$C_5$-alkylen-C(Y)$OR^c$, $C_1$-$C_5$-alkylen-$NR^eR^f$, $C_1$-$C_5$-alkylen-C(Y) $NR^gR^h$, $C_1$-$C_5$-alkylen-$S(O)_mR^d$, $C_1$-$C_5$-alkylen-S $(O)_mNR^eR^f$, $C_1$-$C_5$-alkylen-$NR^iNR^eR^f$,
heterocyclyl, $C_3$-$C_{10}$-cycloalkyl, $C_3$-$C_{10}$-cycloalkenyl, hetaryl, aryl, heterocyclyl-$C_1$-$C_5$-alkyl, $C_3$-$C_{10}$-cycloalkyl-$C_1$-$C_5$-alkyl, $C_3$-$C_{10}$-cycloalkenyl-$C_1$-$C_5$-alkyl, hetaryl-$C_1$-$C_5$-alkyl, aryl-$C_1$-$C_5$-alkyl, wherein the cyclic moieties are unsubstituted or substituted by one or more identical or different substituents $R^y$;
groups -D-E, wherein
D is a direct bond, $C_1$-$C_6$-alkylene, $C_2$-$C_6$-alkenylene, or $C_2$-$C_6$-alkynylene, which carbon chains are unsubstituted or substituted by one or more identical or different substituents $R^n$, and
E is a non-aromatic 3- to 12-membered carbo- or heterocycle, which heterocycles contains one or more heteroatoms selected from N—$R^1$, O, and S, wherein S is oxidized or non-oxidized, and wherein the carbo- or heterocycle is substituted by one or more identical or different substituents $R^n$;
and
groups -A-$SO_m$-G, wherein
A is $C_1$-$C_6$-alkylene, $C_2$-$C_6$-alkenylene and $C_2$-$C_6$-alkynylene, wherein the aliphatic groups are unsubstituted or substituted by one or more identical or different substituents $R^p$, and
G is $C_1$-$C_4$-haloalkyl or $C_3$-$C_6$-cycloalkyl, which groups are unsubstituted or substituted by halogen;
or
$R^4$ and $R^5$ together with the carbon atom to which they are attached form a 3- to 12-membered non-aromatic carbo- or heterocycle, which heterocycle contains one or more heteroatoms selected from N—$R^1$, O, and S, wherein S oxidized or non-oxidized, and wherein the carbon- or heterocycle is substituted by one or more identical or different substituents $R^j$;
and wherein
$R^a$, $R^b$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_3$-$C_6$-cycloalkenyl, $C_3$-$C_6$-cycloalkenylmethyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, aryl, hetaryl, aryl-$C_1$-$C_4$-alkyl and hetaryl-$C_1$-$C_4$-alkyl, wherein the cyclic moieties are unsubstituted or substituted by one or more identical or different substituents selected from halogen, CN, $C(O)NH_2$, $NO_2$, $C_1$-$C_4$-alkoxy, and $C_1$-$C_4$-haloalkoxy;
$R^c$ is selected from H, $C_3$-$C_{10}$-cycloalkyl, $C_3$-$C_{10}$-cycloalkylmethyl, $C_3$-$C_{10}$-halocycloalkyl, $C_3$-$C_6$-cycloalkenyl, $C_3$-$C_6$-cycloalkenylmethyl, $C_3$-$C_6$-halocycloalkenyl, $C_2$-$C_{10}$-alkenyl, $C_2$-$C_{10}$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, aryl, hetaryl, aryl-$C_1$-$C_4$-alkyl and hetaryl-$C_1$-$C_4$-alkyl, wherein the cyclic moieties are unsubstituted or substituted by one or more identical or different substituents selected from halogen, CN, $C(O)NH_2$, $NO_2$, $C_1$-$C_4$-haloalkyl, $C_1$-$C_4$-alkoxy and $C_1$-$C_4$-haloalkoxy; or
$R^c$ together with the C(Y)O group forms a salt $[C(Y)O]^-NR_4^+$, $[C(Y)O]^-M_a^+$ or $[C(Y)O]^{-1/2}M_{ea}^{2+}$, wherein $M_a$ is an alkali metal and $M_{ea}$ is an alkaline earth metal, and wherein the substituents R at the nitrogen atom are independently of each other selected from H, $C_1$-$C_{10}$-alkyl, phenyl, and phenyl-$C_1$-$C_4$-alkyl;

$R^d$ is selected from $C_1$-$C_4$-alkoxy, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_3$-$C_6$-cycloalkenyl, $C_3$-$C_6$-cycloalkenylmethyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, aryl, hetaryl, aryl-$C_1$-$C_4$-alkyl and hetaryl-$C_1$-$C_4$-alkyl, wherein the cyclic moieties are unsubstituted or substituted by one or more identical or different substituents from halogen, CN, C(O)NH$_2$, NO$_2$, $C_1$-$C_4$-alkyl, $C_1$-$C_4$-haloalkyl, $C_1$-$C_4$-alkoxy, and $C_1$-$C_4$-haloalkoxy;

$R^e$, $R^f$ are independently of each other selected from H, $C_1$-$C_4$-haloalkyl, $C_3$-$C_6$-cycloalkyl, $C_3$-$C_6$-cycloalkyl methyl, $C_3$-$C_6$-halocycloalkyl, $C_3$-$C_6$-cycloalkenyl, $C_3$-$C_6$-cycloalkenylmethyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, heterocyclyl, heterocyclyl-$C_1$-$C_4$-alkyl, heterocyclylcarbonyl, heterocyclylsulfonyl, aryl, arylcarbonyl, arylsulfonyl, hetaryl, hetarylcarbonyl, hetarylsulfonyl, aryl-$C_1$-$C_4$-alkyl, and hetaryl-$C_1$-$C_4$-alkyl, wherein the cyclic moieties are unsubstituted or substituted by one or more substituents which, independently of each other, are selected from halogen, CN, C(O)NH$_2$, NO$_2$, $C_1$-$C_4$-haloalkyl, $C_1$-$C_4$-alkoxy, and $C_1$-$C_4$-haloalkoxy; or $R^e$ and $R^f$ together with the N atom to which they are bonded form a 5- or 6-membered, saturated or unsaturated heterocycle, which may contain a further heteroatom selected from O, S and N as a ring member atom, and wherein the heterocycle is unsubstituted or substituted by one or more identical or different substituents selected from halogen, CN, C(O)NH$_2$, NO$_2$, $C_1$-$C_4$-haloalkyl, $C_1$-$C_4$-alkoxy, and $C_1$-$C_4$-haloalkoxy;

$R^g$, $R^h$ are independently of each other selected from H, $C_1$-$C_4$-alkyl, $C_1$-$C_4$-haloalkyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, aryl, hetaryl, aryl-$C_1$-$C_4$-alkyl and hetaryl-$C_1$-$C_4$-alkyl, wherein the cyclic moieties are unsubstituted or substituted by one or more, identical or different substituents selected from halogen, CN, C(O)NH$_2$, NO$_2$, $C_1$-$C_4$-alkyl, $C_1$-$C_4$-haloalkyl, $C_1$-$C_4$-alkoxy, and $C_1$-$C_4$-haloalkoxy;

$R^i$ is selected from H, $C_3$-$C_6$-cycloalkyl, $C_3$-$C_6$-cycloalkylmethyl, $C_3$-$C_6$-halocycloalkyl, $C_3$-$C_6$-cycloalkenyl, $C_3$-$C_6$-cycloalkenylmethyl, $C_3$-$C_6$-halocycloalkenyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, aryl, and aryl-$C_1$-$C_4$-alkyl, wherein the aryl ring is unsubstituted or substituted by one or more identical or different substituents selected from halogen, CN, C(O)NH$_2$, NO$_2$, $C_1$-$C_4$-alkyl, $C_1$-$C_4$-haloalkyl, $C_1$-$C_4$-alkoxy and $C_1$-$C_4$-haloalkoxy;

$R^j$ is halogen, OH, CN, C(O)NH$_2$, NO$_2$, $C_1$-$C_{10}$haloalkoxy, benzyloxy, S(O)$_m$R$^k$, $C_3$-$C_6$-cycloalkyl, or a 3- to 6-membered heterocycle, which contains one or more heteroatoms selected from N—R$^l$, O, and S, wherein S is oxidized or non-oxidized, which R$^j$ groups are unsubstituted or substituted by one or more identical or different substituents R$^m$, and wherein two groups R$^j$ connected to the same or adjacent ring atoms may together form a 3- to 6-membered carbo- or heterocycle, which heterocycle contains one or more heteroatoms selected from N—R$^l$, O, and S, wherein S is oxidized or non-oxidized, and wherein the cyclic groups are unsubstituted or substituted by one or more identical or different substituents R$^m$;

$R^k$ is H, $C_1$-$C_4$-alkyl, $C_1$-$C_4$-haloalkyl, or $C_3$-$C_6$-cycloalkyl, wherein the cyclic group is unsubstituted or substituted by one or more identical or different substituents R$^1$;

$R^1$ is H, halogen, $C_1$-$C_4$-alkyl, $C_1$-$C_4$-alkylcarbonyl, or $C_1$-$C_4$-alkoxycarbonyl;

$R^m$ is halogen, OH, CN, C(O)NH$_2$, NO$_2$, $C_1$-$C_4$-alkyl, $C_3$-$C_6$-cycloalkyl, $C_1$-$C_4$-alkoxy, $C_1$-$C_4$-haloalkoxy, or S(O)$_m$R$^k$;

$R^n$ is halogen, CN, C(Y)OR$^c$, C(O)NH$_2$, NO$_2$, $C_1$-$C_4$-haloalkyl, $C_2$-$C_6$-alkenyl, $C_2$-$C_6$-alkynyl, $C_3$-$C_6$-cycloalkyl, $C_3$-$C_6$-cycloalkenyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkyliden, or S(O)$_m$R$^o$; or two adjacent groups R$^n$ together with the atoms to which they are bonded form a 3- to 8-membered carbo- or heterocycle, which heterocycles contains one or more heteroatoms selected from N—R$^l$, O, and S, wherein S is oxidized or non-oxidized, and wherein the cyclic R$^n$ moieties are unsubstituted or substituted by halogen, R$^o$, or R$^l$;

$R^o$ is H, $C_3$-$C_6$-cycloalkyl, or $C_1$-$C_4$-alkoxy;

$R^p$ is halogen, CN, C(O)NH$_2$, NO$_2$, $C_3$-$C_6$-cycloalkyl, $C_1$-$C_4$-alkoxy, or $C_1$-$C_2$-haloalkoxy; or two groups R$^p$ together form a 3- to 6-membered carbo- or heterocyclic ring, which heterocycle contains one or more heteroatoms selected from N—R$^l$, O, and S, wherein S is oxidized or non-oxidized, and wherein the cyclic groups are unsubstituted or substituted by one or more identical or different substituents R$^q$;

$R^q$ is halogen, CN, C(O)NH$_2$, NO$_2$, $C_1$-$C_4$-alkyl, $C_1$-$C_4$-haloalkyl, $C_3$-$C_6$-cycloalkyl, $C_1$-$C_4$-alkoxy, or $C_1$-$C_4$-haloalkoxy;

$R^x$ is halogen, CN, C(Y)OR$^c$, C(Y)NR$^g$R$^h$, NO$_2$, $C_1$-$C_4$-alkyl, $C_1$-$C_4$-haloalkyl, $C_1$-$C_4$-alkoxy, $C_1$-$C_4$-haloalkoxy, S(O)$_m$R$^d$, S(O)$_m$NR$^e$R$^f$, $C_1$-$C_5$-alkylen-NHC(O)OR$^c$, $C_1$-$C_{10}$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, 5- to 7-membered heterocyclyl, 5- or 6-membered hetaryl, aryl, $C_3$-$C_6$-cycloalkoxy, 3- to 6-membered heterocyclyoxy, or aryloxy, wherein the cyclic moieties are unsubstituted or substituted by one or more, identical or different radicals R$^y$; and $R^y$ is halogen, CN, C(Y)OR$^c$, C(Y)NR$^g$R$^h$, NO$_2$, $C_1$-$C_4$-alkyl, $C_1$-$C_4$-haloalkyl, $C_1$-$C_4$-alkoxy, $C_1$-$C_4$-haloalkoxy, benzyloxymethyl, S(O)$_m$R$^d$, S(O)$_m$NR$^e$R$^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, or $C_1$-$C_4$-alkoxy-$C_1$-$C_4$-alkyl;

and wherein

Y is O or S; Y$^1$ is O, S, or N—R$^{1a}$; R$^{1a}$ is H, $C_1$-$C_{10}$-alkyl, $C_3$-$C_{12}$-cycloalkyl, aryl, or hetaryl; and m is 0, 1 or 2.

The process as defined above is suitable for providing a variety of N-substituted pyrazole compounds V.

The process also provides the desired pyrazole compounds V regioselectively, which is particularly relevant, if the pyrazole compounds V are 3- or 5-substituted or substituted with different substituents in the 3- and 5-position. Regioselectivity is possible due to the fact that the positions of the substituents are already predefined in the pyrazole precursors IV, which are then cyclized to give the pyrazole compounds V.

The process is also cost-effective and suitable for large scale applications in view of the fact that the cyclization reaction can be performed catalytically with hydrogen as a cheap reducing agent.

However, it has been discovered that the use of hydrogen as a reducing agent in the presence of a hydrogenation catalyst may also result in an undesired side reaction. In particular, it has been observed that the C=N-bond of the hydrazone group of the pyrazole precursors IV is often completely reduced before the cyclization reaction. Accordingly, the following reaction sequence takes place giving the undesired NH-pyrazoles $V^H$ via the NH-pyrazole precursors $IV^H$, instead of the desired N-substituted pyrazole compounds V.

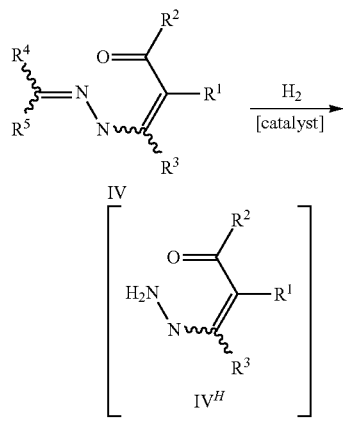

It has surprisingly been found that this undesired side reaction can effectively be reduced, if the pyrazole precursor IV is provided in a reaction mixture comprising as components not only a hydrogenation catalyst, but also an acid selected from Brønsted acids, ammonium salts of Brønsted acids, and Lewis acids, and a protic solvent. Due to the presence of the acid and the protic solvent, it can be avoided that the C=N-bond of the hydrazone group of the pyrazole precursors IV is completely reduced before the cyclization reaction. Accordingly, the above reaction sequence giving the undesired NH-pyrazoles $V^H$ via the NH-pyrazole precursors $IV^H$ is largely suppressed. Instead, the pyrazole precursors IV are to a large extent only partly reduced at the C=N-bond and then directly cyclized to give the desired N-substituted pyrazole compounds V according to the following equation.

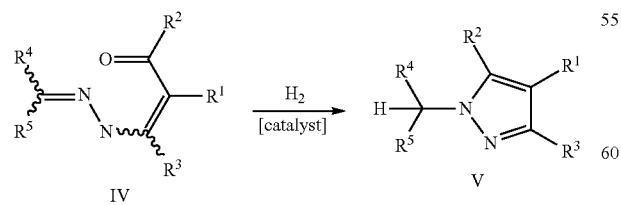

Thus, it has been found that if the cyclization of the pyrazole precursors IV is performed according to the present invention, a large excess of the desired N-substituted pyrazole compounds V can be obtained compared to the undesired NH-pyrazole compounds V*. Accordingly, high yields of the pyrazole compounds V can be obtained.

In view of the above, the process of the present invention provides for the advantage that the cyclization of pyrazole precursors IV regioselectively provides the desired N-substituted pyrazole compounds V with hydrogen as a cheap reducing agent and a catalyst system, which suppresses undesired side reactions to an extent that high yields of the desired N-substituted pyrazole compounds V can be obtained.

It is another advantage of the process of the present invention that the pyrazole precursors IV can be obtained from readily and cheaply available starting materials. In particular, the pyrazole precursors IV may be obtained by reacting a hydrazone compound II (the compound II itself being obtainable by reacting a suitable carbonyl compound I with hydrazine), with an α,β-unsaturated carbonyl compound of formula III.

In view of the above, certain preferred embodiments of the invention relate to a process, wherein the hydrazone substituted α,β-unsaturated carbonyl compound of formula IV

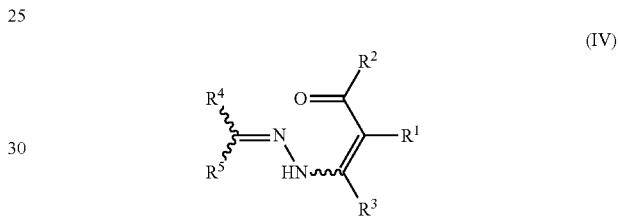

is prepared by reacting an α,β-unsaturated carbonyl compound of formula III

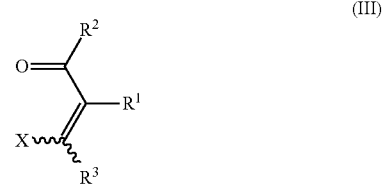

with a hydrazone compound of formula II

wherein

X is halogen, OH, $C_1$-$C_{10}$-alkoxy, $C_3$-$C_{10}$-cycloalkoxy, $C_1$-$C_{10}$-alkyl-C(O)O—, $C_1$-$C_{10}$-alkyl-S(O)$_2$O—, $C_1$-$C_{10}$-haloalkyl-S(O)$_2$O—, phenyl-S(O)$_2$O—, tolyl-S(O)$_2$O—, ($C_1$-$C_{10}$-alkyloxy)$_2$P(O)O—, $C_1$-$C_{10}$-alkylthio, $C_3$-$C_{10}$-cycloalkylthio, $C_1$-$C_{10}$-alkyl-C(O)S—, NH$_2$, $C_1$-$C_{10}$-alkylamino, $C_1$-$C_{10}$-dialkylamino, morpholino, N-methylpiperazino, or aza-$C_3$-$C_{10}$-cycloalkyl; and is preferably OCH$_2$CH$_3$;

and $R^1$, $R^2$, $R^3$, $R^4$ and $R^5$ are as defined above.

Furthermore, certain more preferred embodiments of the invention relate to a process, wherein the above hydrazone compound of formula II is prepared by reacting a carbonyl compound of formula I

(I)

with hydrazine or a salt thereof,
wherein $R^4$ and $R^5$ are as defined above.

In connection with the preparation of the pyrazole precursors IV, it has surprisingly been found that it is not required to purify the pyrazole precursors IV before the cyclization reaction to give the pyrazole compounds V, so that a one-pot reaction according to the following equation may be performed.

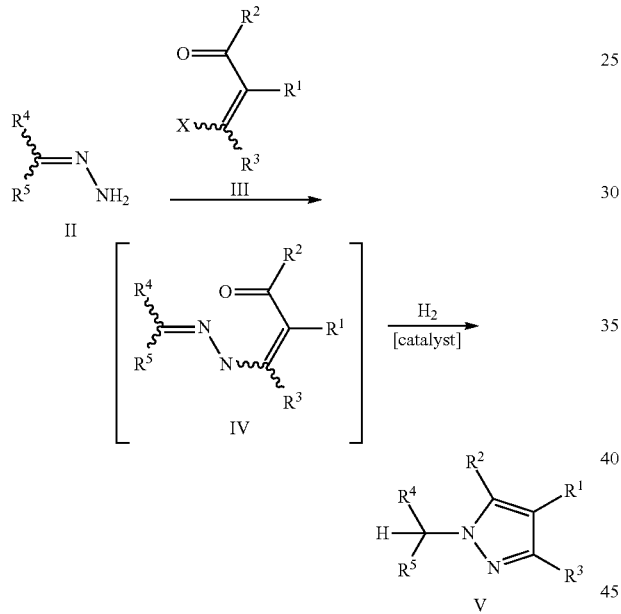

In connection with the one-pot reaction, it has been found that it is not necessarily required to remove the solvent, wherein the pyrazole precursor IV is prepared, even if said solvent is an aprotic solvent. Rather, it can be sufficient to simply add a protic solvent, preferably ethanol, before the cyclization reaction. In addition, it is of course required to add a hydrogenation catalyst, which preferably comprises palladium or platinum. Furthermore, an acid selected from Brønsted acids, ammonium salts of Brønsted acids, and Lewis acids may be added to increase the yields of the pyrazole compound V.

Of particular relevance in connection with the present invention are pyrazole compounds V and pyrazole precursors IV, wherein
$R^1$ is $C(O)OCH_2CH_3$; $R^2$ is $CH_3$; $R^3$ is H; $R^4$ is $CH(CH_3)_2$; and $R^5$ is $CH_3$.

In connection with the above mentioned one-pot reaction, the present invention therefore also relates to a composition comprising (1) a compound of formula IV

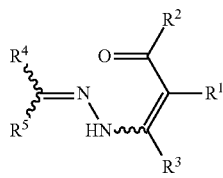

(IV)

wherein
$R^1$ is $C(O)OCH_2CH_3$; $R^2$ is $CH_3$; $R^3$ is H; $R^4$ is $CH(CH_3)_2$; and $R^5$ is $CH_3$;

and (2) at least one component selected from
(a) a hydrogenation catalyst comprising palladium or platinum,
(b) an acid selected from Brønsted acids, ammonium salts of Brønsted acids, and Lewis acids, and
(c) ethanol.

It is to be understood that the pyrazole compounds V, which are prepared according to the process of the present invention, preferably comprise a substituent $R^1$, which is suitable for further coupling reactions, in particular amidation reactions. Preferably, the pyrazole compounds V are selected from pyrazole compounds Va, Vb, or Vc as depicted below, wherein $R^2$, $R^3$, $R^4$, and $R^5$ are as defined above, and wherein $R^c$ in formula Va is $C_1$-$C_4$-alkyl or aryl-$C_1$-$C_4$-alkyl.

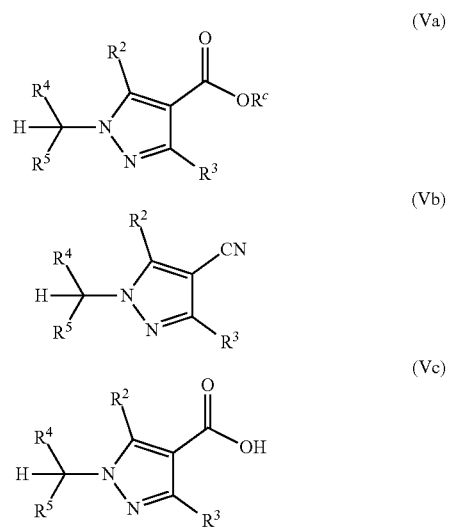

Certain preferred embodiments of the invention relate to a process, wherein the compound of formula V is a compound of formula Va or Vb, and wherein said compound of formula Va or Vb is in a further reaction step converted into a compound of formula Vc, wherein $R^2$, $R^3$, $R^4$ and $R^5$ are as defined above, and wherein $R^c$ in formula Va is $C_1$-$C_4$-alkyl or aryl-$C_1$-$C_4$-alkyl.

Furthermore, certain preferred embodiments of the invention relate to a process, wherein the compound of formula Vc is in a further reaction step converted into a compound of formula VI

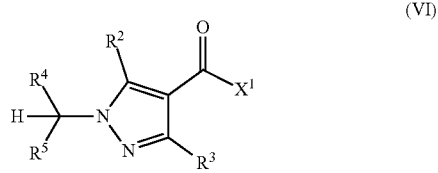

(VI)

wherein $X^1$ is a leaving group, preferably a leaving group selected from active esters, azide and halogens, particularly preferably p-nitrophenoxy, pentafluorophenoxy or Cl, and wherein $R^2$, $R^3$, $R^4$, and $R^5$ are as defined above.

Moreover, certain preferred embodiments of the invention relate to a process, wherein the above compound of formula VI is in a further reaction step converted into a compound of formula VIII

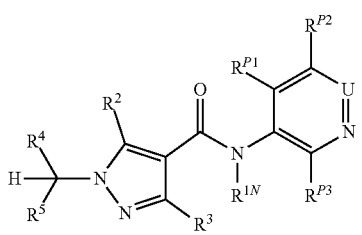

(VIII)

by reacting it with a compound of formula VII

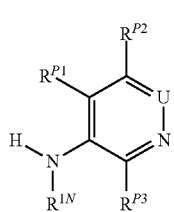

(VII)

wherein $R^2$, $R^3$, $R^4$, and $R^5$ are as defined above, and wherein

U is N or $CR^U$;

$R^{P1}$, $R^{P2}$, $R^{P3}$, and $R^U$ are independently of each other selected from H, halogen, $C_1$-$C_4$-alkyl, $C_1$-$C_3$-haloalkyl, $C_1$-$C_4$-alkoxy, $C_1$-$C_3$-haloalkoxy, $C_1$-$C_4$-alkylthio, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl; and $R^{1N}$ is H, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_1$-$C_4$-alkoxy-$C_1$-$C_4$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_1$-$C_5$-alkylen-CN, $OR^a$, $C_1$-$C_5$-alkylen-$OR^a$, $C(Y)R^b$, $C_1$-$C_5$-alkylen-$C(Y)R^b$, $C(Y)OR^c$, $C_1$-$C_5$-alkylen-$C(Y)OR^c$, $S(O)_2R^d$, $NR^eR^f$, $C_1$-$C_5$-alkylen-$NR^eR^f$, $C(Y)NR^gR^h$, $C_1$-$C_5$-alkylen-$C(Y)NR^gR^h$, $S(O)_mNR^eR^f$, $C(Y)NR^iNR^eR^f$, $C_1$-$C_5$-alkylen-$S(O)_2R^d$, $C_1$-$C_5$-alkylen-$S(O)_mNR^eR^f$, $C_1$-$C_5$-alkylen-$C(Y)NR^iNR^eR^f$, aryl, heterocyclyl, hetaryl, aryl-$C_1$-$C_5$-alkyl, $C_3$-$C_{10}$-cycloalkyl-$C_1$-$C_5$-alkyl, heterocyclyl-$C_1$-$C_5$-alkyl or hetaryl-$C_1$-$C_5$-alkyl, wherein the cyclic moieties may be unsubstituted or may be substituted by 1, 2, 3, 4, or 5 identical or different substituents selected from the radicals $R^y$ and $R^x$, and wherein preferably U is N or CH; $R^{P1}$, $R^{P2}$, $R^{P3}$ are H; and $R^{1N}$ is H, $C_1$-$C_2$-alkyl or $C_1$-$C_2$-alkoxy-$C_1$-$C_2$-alkyl.

Thus, the pyrazole compounds Va, Vb, and Vc may be further converted according to the following reaction sequence:

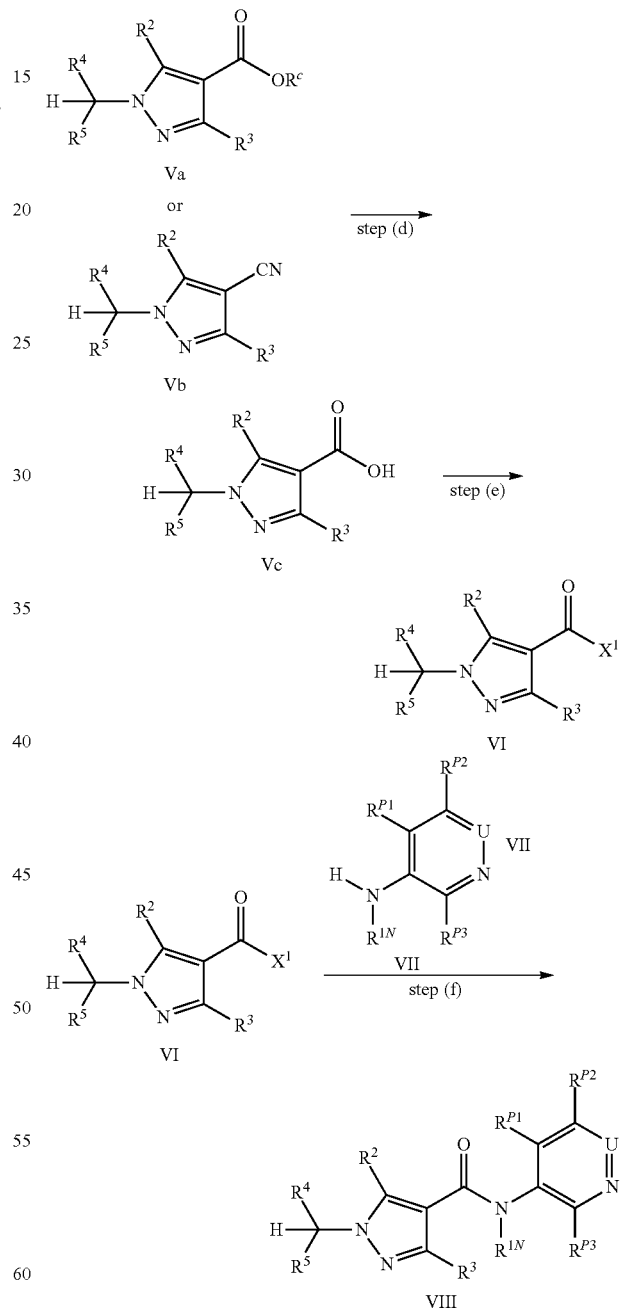

Further embodiments of the present invention can be found in the claims, the description and the examples. It is to be understood that the features mentioned above and those still to be illustrated below of the subject matter of the invention are preferred not only in the respective given combination, but also in other combinations without leaving the scope of the invention.

In the context of the present invention, the terms used generically are each defined as follows:

The term "compound(s) according to the invention" in the context of the compounds of formulae I, II, III, IV, V, Va, Vb, Vc, VI, VII and VIII as defined hereinabove and hereinafter comprises the compound(s) as defined herein as well as stereoisomers, salts, tautomers or N-oxides thereof. The term "compound(s) of the present invention" is to be understood as equivalent to the term "compound(s) according to the invention".

It is noted that the compounds of formula IV of the invention may also be referred to as α,β-unsaturated carbonyl compounds of formula IV or as pyrazole precursors IV or precursors IV. Furthermore, the compounds of formula V, may be referred to as pyrazole compounds V or pyrazoles V.

N-oxides of the compounds of the present invention can only be obtained, if the compounds contain a nitrogen atom, which may be oxidized. This is principally the case for the compounds of formulae II, IV, V, Va, Vb, Vc, VI, VII and VIII, but not necessarily the case for compounds of formulae I and III. Accordingly, the term "compound(s) according to the invention" will only cover stereoisomers, salts and tautomers of the compounds of formulae I and III, if these compounds do not contain a nitrogen substituent, which would allow for the formation of an N-oxide. N-oxides may principally be prepared by standard methods, e.g. by the method described in Journal of Organometallic Chemistry 1989, 370, 17-31. However, it is preferred according to the invention that the intermediate compounds I, II, III and IV in the preparation of the compounds of formula V are not present in the form of the N-oxides. Furthermore, if it is desired to convert compounds of formula Va or Vb into compounds of formula Vc, or to convert compounds of formula Vc into compounds of formula VI, or to convert compounds of formula VI into compounds of formula VIII, it is also preferred that the compounds are not present in the form of N-oxides. On the other hand, under certain reaction conditions, it cannot be avoided that N-oxides are formed at least intermediary.

Stereoisomers of the compounds of formulae I, II, III, IV, V, Va, Vb, Vc, VI, VII and VIII will be present, if the compounds contain one or more centers of chirality in the substituents. In this case, the compounds will be present in the form of different enantiomers or diastereomers, if more than one center of chirality is present. The compounds of the present invention cover every possible stereoisomer, i.e. single enantiomers or diastereomers, as well as mixtures thereof. With regard to the compounds of formula V, it is noted that a center of chirality is also present in the generic formula, if the substituents $R^4$ and $R^5$ are different from H and different from each other. Said center of chirality is newly formed, when the compounds of formula V are prepared from the compounds of formula IV. In particular, the sp$^2$-hybridized carbon atom, to which the substituents $R^4$ and $R^5$ are attached in the compounds of formula IV, may be attacked from two sides during the hydrogenation, so that principally two configurations can be obtained at the resulting sp$^3$-hybridized carbon atom. The two possible stereoisomers of the compounds of formula V, V:SI-A and V:SI-B, which can be obtained according to the process according to the present invention, are depicted below.

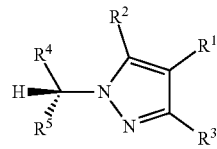

(V:SI-A)

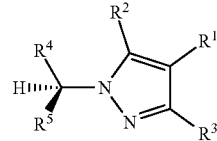

(V:SI-B)

Analogous stereoisomers are also possible for the compounds of formula Va, Vb, Vc, VI and VIII. Thus, if the substituents $R^4$ and $R^5$ are different from H and different from each other, so that a center of chirality is present, the generic formulae V, Va, Vb, Vc, VI and VIII as used herein are in each case intended to cover two stereoisomers analogous to the two stereoisomers as depicted above. For reasons of clarity, it is not distinguished between the two stereoisomers of the generic formulae V, Va, Vb, Vc, VI and VIII throughout the specification. Instead the —CR$^4$R$^5$H group is depicted without any indication regarding the three dimensional structure, but it is to be understood that the generic formulae V, Va, Vb, Vc, VI and VIII in each case embrace both possible stereoisomers, if the —CR$^4$R$^5$H group is chiral.

Geometric isomers of the compounds of the present invention are usually possible, if the compounds contain at least one carbon-carbon or carbon-nitrogen double bond because E- and Z-isomers of the compounds may then be present. The compounds of the present invention cover every possible geometric isomer, i.e. single E- or Z-isomers as well as mixtures thereof. With regard to the compounds of formulae II, III and IV, it is noted that a carbon-carbon double bond and/or a carbon-nitrogen double bond is already present in the generic formula. As in each case the E- and Z-isomers are both intended to be covered, the generic formulae are depicted with wavy lines to the substituents, which indicates that the two substituents at one sp$^2$-hybridized carbon atom may be present in each position. The possible E- and Z-isomers for the compounds of formula II (i.e. II:GI-A$^1$ and II:GI-B$^1$), III (i.e. III:GI-A$^2$ and III:GI-B$^2$) and IV (i.e. IV:GI-A$^1$A$^2$, IV:GI-B$^1$A$^2$, IV:GI-A$^1$B$^2$ and IV:GI-B$^1$B$^2$) are depicted below.

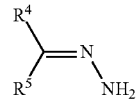

(II:GI-A$^1$)

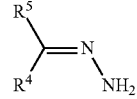

(II:GI-B$^1$)

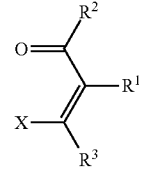

(III:GI-A$^2$)

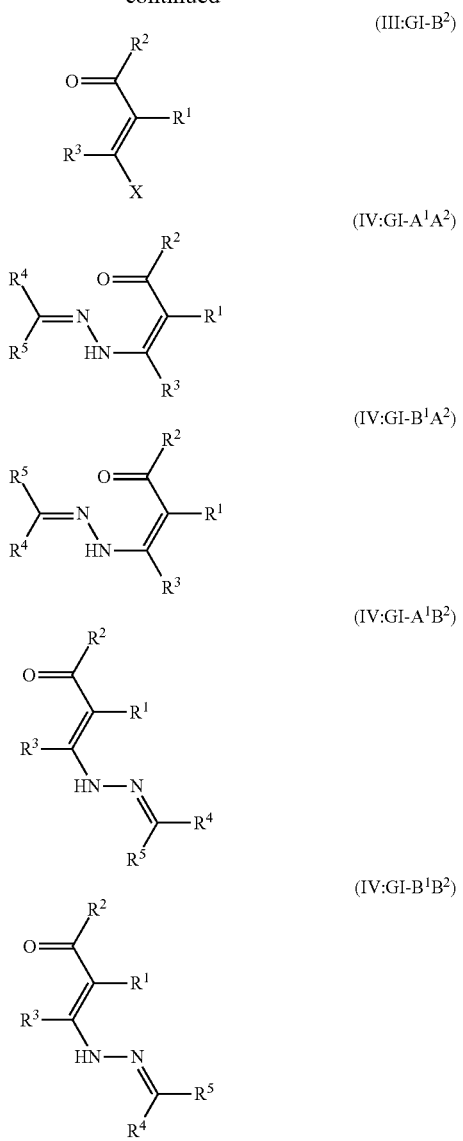

Thus, if E- and Z-isomers are possible, the generic formulae II, III and IV as used herein are in each case intended to cover all geometric isomers as depicted above, which is indicated by the wavy lines to the substituents in the generic formulae.

Tautomers of the compounds of formulae I, II, III, IV, V, Va, Vb, Vc, VI, VII and VIII include keto-enol tautomers, imine-enamine tautomers, amide-imidic acid tautomers and the like. Such tautomerism is possible, e.g., for the generic formulae I, II, III, IV and VIII (if $R^{1N}$ is H). Depending on the substituents, which are defined for the compounds of formulae I, II, III, IV, V, Va, Vb, Vc, VI, VII and VIII, further tautomers may be formed. The compounds of the present invention cover every possible tautomer.

Depending on the acidity or basicity as well as the reaction conditions, the compounds of formulae I, II, III, IV, V, Va, Vb, Vc, VI, VII and VIII may be present in the form of salts. Such salts will typically be obtained by reacting the compound with an acid, if the compound has a basic functionality such as an amine, or by reacting the compound with a base, if the compound as an acidic functionality such as a carboxylic acid group. For example, the compounds of formula Vb include 4-pyrazole carboxylic acid salts, wherein the cation stems from the base, with which the 4-pyrazole carboxylic acid has been reacted to give an anionic carboxylate. If a carboxylic acid group COOH is present in the form of a carboxylate, said anion may be referred to as $[C(O)O]^-$, wherein the negative charge is typically delocalized over the two oxygen atoms of the carboxylate group. On the other hand, the cationic charge of an ammonium cation, which may be formed from an amino group in the presence of an acid, is typically not delocalized.

Cations, which stem from a base, with which the compounds of the present invention are reacted, are e.g. alkali metal cations $M_a^+$, alkaline earth metal cations $M_{ea}^{2+}$ or ammonium cations $NR_4^+$, wherein the alkali metals are preferably sodium, potassium or lithium and the alkaline earth metal cations are preferably magnesium or calcium, and wherein the substituents R of the ammonium cation $NR_4^+$ are preferably independently selected from H, $C_1$-$C_{10}$-alkyl, phenyl and phenyl-$C_1$-$C_2$-alkyl.

Anions, which stem from an acid, with which the compounds of the present invention have been reacted, are e.g. chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate.

The compounds of the invention may be in the form of solids or liquids. If the compounds are present as solids, the compounds may be amorphous or may exist in one or more different crystalline forms. The compounds of the present invention cover mixtures of different crystalline forms of the respective compounds as well as amorphous or crystalline salts thereof.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkylamino, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkylcarbonyl, haloalkoxycarbonyl, haloalkylthio, haloalkylsulfonyl, haloalkylsulfinyl, haloalkoxy and haloalkoxyalkyl, denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bonded via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "alkoxyalkyl" as used herein refers to alkyl usually comprising 1 to 10, frequently 1 to 4, preferably 1 to 2 carbon atoms, wherein 1 carbon atom is substituted by an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluoroethoxy, 2,2,2-trichloroethoxy, pentafluoroethoxy and the like.

The term "alkylthio "(alkylsulfanyl: alkyl-S—)" as used herein refers to a straight-chain or branched saturated alkyl group having 1 to 10 carbon atoms, preferably 1 to 4 carbon atoms (=$C_1$-$C_4$-alkylthio), more preferably 1 to 3 carbon atoms, which is attached via a sulfur atom.

The term "haloalkylthio" as used herein refers to an alkylthio group as mentioned above wherein the hydrogen atoms are partially or fully substituted by fluorine, chlorine, bromine and/or iodine.

The term "alkylsulfinyl" (alkylsulfoxyl: $C_1$-$C_6$-alkyl-S (=O)—), as used herein refers to a straight-chain or branched saturated alkyl group (as mentioned above) having 1 to 10 carbon atoms, preferably 1 to 4 carbon atoms (=$C_1$-$C_4$-alkylsulfinyl), more preferably 1 to 3 carbon atoms bonded through the sulfur atom of the sulfinyl group at any position in the alkyl group.

The term "haloalkylsulfinyl" as used herein refers to an alkylsulfinyl group as mentioned above wherein the hydrogen atoms are partially or fully substituted by fluorine, chlorine, bromine and/or iodine.

The term "alkylsulfonyl" (alkyl-S(=O)$_2$-) as used herein refers to a straight-chain or branched saturated alkyl group having 1 to 10 carbon atoms, preferably 1 to 4 carbon atoms (=$C_1$-$C_4$-alkylsulfonyl), preferably 1 to 3 carbon atoms, which is bonded via the sulfur atom of the sulfonyl group at any position in the alkyl group.

The term "haloalkylsulfonyl" as used herein refers to an alkylsulfonyl group as mentioned above wherein the hydrogen atoms are partially or fully substituted by fluorine, chlorine, bromine and/or iodine.

The term "alkylcarbonyl" refers to an alkyl group as defined above, which is bonded via the carbon atom of a carbonyl group (C=O) to the remainder of the molecule.

The term "haloalkylcarbonyl" refers to an alkylcarbonyl group as mentioned above, wherein the hydrogen atoms are partially or fully substituted by fluorine, chlorine, bromine and/or iodine.

The term "alkoxycarbonyl" refers to an alkylcarbonyl group as defined above, which is bonded via an oxygen atom to the remainder of the molecule.

The term "haloalkoxycarbonyl" refers to an alkoxycarbonyl group as mentioned above, wherein the hydrogen atoms are partially or fully substituted by fluorine, chlorine, bromine and/or iodine.

The term "alkenyl" as used herein denotes in each case a singly unsaturated hydrocarbon radical having usually 2 to 10, frequently 2 to 6, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein refers to an alkenyl group as defined above, wherein the hydrogen atoms are partially or totally replaced with halogen atoms.

The term "alkynyl" as used herein denotes in each case a singly unsaturated hydrocarbon radical having usually 2 to 10, frequently 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "cycloalkyl" as used herein and in the cycloalkyl moieties of cycloalkoxy and cycloalkylthio denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "halocycloalkyl" as used herein and in the halocycloalkyl moieties of halocycloalkoxy and halocycloalkylthio denotes in each case a monocyclic cycloaliphatic radical having usually from 3 to 10 C atoms or 3 to 6 C atoms, wherein at least one, e.g. 1, 2, 3, 4, or 5 of the hydrogen atoms, are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkoxy" refers to a cycloalkyl group as defined above, which is bonded via an oxygen atom to the remainder of the molecule.

The term "halocycloalkoxy" refers to a halocycloalkyl group as defined above, which is bonded via an oxygen atom to the remainder of the molecule.

The term "cycloalkylthio" refers to a cycloalkyl group as defined above, which is bonded via a sulfur atom to the remainder of the molecule.

The term "halocycloalkylthio" refers to a halocycloalkyl group as defined above, which is bonded via a sulfur atom to the remainder of the molecule.

The term "cycloalkylalkyl" refers to a cycloalkyl group as defined above which is bonded via an alkyl group, such as a $C_1$-$C_5$-alkyl group or a $C_1$-$C_4$-alkyl group, in particular a methyl group (=cycloalkylmethyl), to the remainder of the molecule.

The term "cycloalkenyl" as used herein and in the cycloalkenyl moieties of cycloalkenyloxy and cycloalkenylthio denotes in each case a monocyclic singly unsaturated non-aromatic radical having usually from 3 to 10, e.g. 3, or 4 or from 5 to 10 carbon atoms, preferably from 3- to 8 carbon atoms. Exemplary cycloalkenyl groups include cyclopropenyl, cycloheptenyl or cyclooctenyl.

The term "halocycloalkenyl" as used herein and in the halocycloalkenyl moieties of halocycloalkenyloxy and halocycloalkenylthio denotes in each case a monocyclic singly unsaturated non-aromatic radical having usually from 3 to 10, e.g. 3, or 4 or from 5 to 10 carbon atoms, preferably from 3- to 8 carbon atoms, wherein at least one, e.g. 1, 2, 3, 4, or 5 of the hydrogen atoms, are replaced by halogen, in particular by fluorine or chlorine. Examples are 3,3-difluorocyclopropen-1-yl and 3,3-dichlorocyclopropen-1-yl.

The term "cycloalkenyloxy" refers to a cycloalkenyl group as defined above, which is bonded via an oxygen atom to the remainder of the molecule.

The term "halocycloalkenyloxy" refers to a halocycloalkenyl group as defined above, which is bonded via an oxygen atom to the remainder of the molecule.

The term "cycloalkenylthio" refers to a cycloalkenyl group as defined above, which is bonded via a sulfur atom to the remainder of the molecule.

The term "halocycloalkenylthio" refers to a halocycloalkenyl group as defined above, which is bonded via a sulfur atom to the remainder of the molecule.

The term "cycloalkenylalkyl" refers to a cycloalkenyl group as defined above which is bonded via an alkyl group, such as a $C_1$-$C_5$-alkyl group or a $C_1$-$C_4$-alkyl group, in particular a methyl group (=cycloalkenylmethyl), to the remainder of the molecule.

The term "carbocycle" or "carbocyclyl" includes in general a 3- to 12-membered, preferably a 3- to 8-membered or a 5- to 8-membered, more preferably a 5- or 6-membered mono-cyclic, non-aromatic ring comprising 3 to 12, preferably 3 to 8 or 5 to 8, more preferably 5 or 6 carbon atoms. Preferably, the term "carbocycle" covers cycloalkyl and cycloalkenyl groups as defined above.

The term "heterocycloalkyl" includes in general 3- to 8-membered, in particular 6-membered monocyclic saturated heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

The term "heterocycloalkenyl" includes in general 3- to 8-membered, in particular 6-membered monocyclic singly unsaturated heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

The term "heterocycle" or "heterocyclyl" includes in general 3- to 12-membered, preferably 3- to 8-membered or 5- to 8-membered, more preferably 5- or 6-membered, in particular 6-membered monocyclic heterocyclic non-aromatic radicals. The heterocyclic non-aromatic radicals usually comprise 1, 2, 3, 4, or 5, preferably 1, 2 or 3 heteroatoms selected from N, O and S as ring members, where S-atoms as ring members may be present as S, SO or $SO_2$. Examples of 5- or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S-oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "aryl" includes mono-, bi- or tricyclic aromatic radicals having usually from 6 to 14, preferably 6, 10, or 14 carbon atoms. Exemplary aryl groups include phenyl, naphthyl and anthracenyl. Phenyl is preferred as aryl group.

The term "hetaryl" includes monocyclic 5- or 6-membered heteroaromatic radicals comprising as ring members 1, 2, 3, or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4-, or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3-, or 5-oxazolyl, isoxazolyl, i.e. 3-, 4-, or 5-isoxazolyl, thiazolyl, i.e. 2-, 3- or 5-thiazolyl, isothiazolyl, i.e. 3-, 4-, or 5-isothiazolyl, pyrazolyl, i.e. 1-, 3-, 4-, or 5-pyrazolyl, i.e. 1-, 2-, 4-, or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "heterocyclyloxy", "hetaryloxy", "aryloxy" and "phenoxy" refer to heterocyclyl, hetaryl and aryl as defined above and phenyl, which are bonded via an oxygen atom to the remainder of the molecule.

The terms "heterocyclylsulfonyl", "hetarylsulfonyl", "arylsulfonyl", and "phenylsulfonyl" refer to heterocyclyl, hetaryl and aryl as defined above, and phenyl, respectively, which are bonded via the sulfur atom of a sulfonyl group to the remainder of the molecule.

The terms "heterocyclylcarbonyl", "hetarylcarbonyl", "arylcarbonyl", and "phenylcarbonyl" refer to heterocyclyl, hetaryl and aryl as defined above, and phenyl, respectively, which are bonded via the carbon atom of a carbonyl group (C=O) to the remainder of the molecule.

The terms "heterocyclylalkyl" and "hetarylalkyl" refer to heterocyclyl or hetaryl, respectively, as defined above which are bonded via a $C_1$-$C_5$-alkyl group or a $C_1$-$C_4$-alkyl group, in particular a methyl group (=heterocyclylmethyl or hetarylmethyl, respectively), to the remainder of the molecule.

The terms "arylalkyl" and "phenylalkyl" refer to aryl as defined above and phenyl, respectively, which are bonded via $C_1$-$C_5$-alkyl group or a $C_1$-$C_4$-alkyl group, in particular a methyl group (=arylmethyl or phenylmethyl), to the remainder of the molecule, examples including benzyl, 1-phenylethyl, 2-phenylethyl, etc.

The term "arylalkoxy" and "benzyloxy" refer to arylalkyl as defined above and phenyl-$C_1$-alkyl, respectively, which are bonded via an oxygen atom, to the remainder of the molecule.

The terms "alkylene", "cycloalkylene", "heterocycloalkylene", "alkenylene", "cycloalkenylene", "heterocycloalkenylene" and "alkynylene" refer to alkyl, cycloalkyl, heterocycloalkyl, alkenyl, cycloalkenyl, heterocycloalkenyl and alkynyl as defined above, respectively, which are bonded to the remainder of the molecule, via two atoms, preferably via two carbon atoms, of the respective group, so that they represent a linker between two moieties of the molecule.

The term "cyclic moiety" can refer to any cyclic groups, which are present in the compounds of the present invention, and which are defined above, e.g. cycloalkyl, cycloalkenyl, carbocycle, heterocycloalkyl, heterocycloalkenyl, heterocycle, aryl, hetaryl and the like.

The remarks made below concerning preferred embodiments of the substituents of the compounds of formulae I, II, III, IV, V, Va, Vb, Vc, VI, VII and VIII, are preferred on their own as well as preferably in combination with each other as well in combination with the preferences regarding the process steps of the invention.

In view of the fact that the compounds of formula V of the present invention can be obtained according to the sequence comprising the steps (a) I->II, (b) II+III->IV, and (c) IV->V as described above and herein after, and in view of the fact that the compounds of formula V, if provided e.g. as compounds of formula Va and Vb, may be further converted according to the sequence comprising the steps (d) Va or Vb->Vc, (e) Vc->VI, and (f) VI+VII->VIII as described above and herein after, the substituents, which are preferred for the compounds of formula V will also be preferred for its precursors I, II, III and IV, provided that the substituents are present, and the same substituents will also be preferred for the compounds, which are obtainable from the compounds of formula Va, Vb and Vc, i.e. the compounds of formula VI and VIII, provided that the substituents are present.

The following preferences regarding the substituents therefore not only refer to the compounds of formula V, but also to the compounds of formulae I, II, III, IV, Va, Vb, Vc, VI, VII, and VIII if present. In particular, the preferred substituent meanings refer to the compounds of formula IV and V as used in the essential step (c) of the process of the invention, which is described in further detail below.

The substituent $R^1$ is present in the 4-position of the pyrazole ring of the compounds of formula V. The substituent $R^1$ is also present in the precursors III and IV of the compounds of formula V.

In a preferred embodiment of the invention, $R^1$ is

H, halogen, CN, $NO_2$, $C_1$-$C_{10}$-alkyl, which is unsubstituted, partially or fully halogenated, or substituted by 1, 2 or 3 identical or different substituents $R^x$, or $C(Y)OR^c$, $S(O)_mR^d$, $S(O)_mY^1R^d$, $C_3$-$C_{12}$-cycloalkyl, aryl, or hetaryl, wherein the cyclic moieties are unsubstituted or substituted by 1, 2, 3, 4, or 5 identical or different substituents selected from the radicals $R^y$ and $R^x$;

wherein $R^c$ is H, $C_1$-$C_4$-alkyl or aryl-$C_1$-$C_4$-alkyl, or wherein $R^c$ together with the C(Y)O group forms a salt $[C(Y)O]^-NH_4^+$, $[C(Y)O]^-M_a^+$ or $[C(Y)O]^{-1/2}M_{ea}^{2+}$, wherein $M_a$ is an alkali metal and $M_{ea}$ is an alkaline earth metal;

wherein $R^d$ is $C_1$-$C_4$-alkyl, $C_3$-$C_6$-cycloalkyl, aryl or hetaryl;

wherein Y is O; and wherein $Y^1$ is O or $NR^1a$, wherein $R^{1a}$ is $C_1$-$C_4$-alkyl, $C_3$-$C_6$-cycloalkyl, aryl or hetaryl.

In a more preferred embodiment of the invention, $R^1$ is CN or $C(Y)OR^c$, wherein Y is O and $R^c$ is $C_1$-$C_4$-alkyl or benzyl. In this connection, $R^c$ is preferably ethyl, tert-butyl, or benzyl, and more preferably ethyl or tert-butyl. In a particularly preferred embodiment, $R^1$ is $C(O)OCH_2CH_3$.

The substituent $R^2$ is present in the 5-position of the pyrazole ring of the compounds of formulae V, Va, Vb, Vc, VI and VIII. Furthermore, the substituent $R^2$ is present in the precursors III and IV of the compounds of formula V.

In a preferred embodiment of the invention $R^2$ is $C_1$-$C_{10}$-alkyl, which is unsubstituted, partially or fully halogenated, or substituted by 1, 2 or 3 identical or different substituents $R^x$, $C_3$-$C_{12}$-cycloalkyl, aryl, or hetaryl, wherein the three last mentioned radicals are unsubstituted or substituted by 1, 2, 3, 4, or 5 identical or different substituents selected from the radicals $R^y$ and $R^x$.

In a more preferred embodiment of the invention, $R^2$ is $C_1$-$C_4$-alkyl, which is unsubstituted, or partially or fully halogenated.

It is even more preferred that $R^2$ is $CH_3$, $CH_2CH_3$ or fluoromethyl, and particularly preferred that $R^2$ is $CH_3$, $CF_2H$ or $CF_3$.

In a particularly preferred embodiment, $R^2$ is $CH_3$.

The substituent $R^3$ is present in the 3-position of the pyrazole ring of the compounds of formulae V, Va, Vb, Vc, VI and VIII. Furthermore, the substituent $R^3$ is present in the precursors III and IV of the compounds of formula V.

In a preferred embodiment of the invention $R^3$ is

H, $C_1$-$C_{10}$-alkyl, which is unsubstituted, partially or fully halogenated, or substituted by 1, 2 or 3 identical or different substituents $R^x$, $C_3$-$C_{12}$-cycloalkyl, aryl, or hetaryl, wherein the cyclic moieties are unsubstituted or substituted by 1, 2, 3, 4, or 5 identical or different substituents selected from the radicals $R^y$ and $R^x$.

In a more preferred embodiment of the invention, $R^3$ is H.

As already indicated above, the process according to the present invention is particularly advantageous for regioselectively preparing N-substituted pyrazole compounds, which are 3- or 5-substituted or substituted with different substituents in the 3- and 5-position. Thus, compounds of formula V, wherein $R^3$ and $R^2$ are different from each other are particularly preferred. It is particularly preferred that one of $R^3$ and $R^2$ is H and the other one is different from H. Alternatively, it can be preferred that $R^3$ and $R^2$ are both different from H, and different from each other.

For example, it is preferred that $R^2$ is $CH_3$ and $R^3$ is H.

The substituents $R^4$ and $R^5$ are present in the compounds of formulae I, II, IV, V, Va, Vb, Vc, VI and VIII.

In one preferred embodiment of the invention, $R^4$ is selected from $C_1$-$C_{10}$-alkyl, which is unsubstituted, partially or fully halogenated, or substituted by 1, 2 or 3 identical or different substituents $R^x$, and $C_3$-$C_{10}$-cycloalkyl, which is unsubstituted or substituted by 1, 2, 3, 4, or 5 identical or different substituents $R^y$; and $R^5$ is selected from $C_1$-$C_{10}$-alkyl, which is unsubstituted, partially or fully halogenated, or substituted by 1, 2 or 3 identical or different substituents $R^x$, and $C_3$-$C_{10}$-cycloalkyl, which is unsubstituted or substituted by 1, 2, 3, 4, or 5 identical or different substituents R.

In a more preferred embodiment, $R^4$ is selected from $C_1$-$C_4$-alkyl, which is unsubstituted, partially or fully halogenated, or substituted by 1 or 2 identical or different substituents $R^x$, wherein $R^x$ is selected from CN and $C(O)NH_2$, and $C_3$-$C_6$-cycloalkyl, which is unsubstituted or substituted by 1, 2 or 3 identical or different substituents $R^y$, wherein $R^y$ is selected from halogen, CN and $C(O)NH_2$; and $R^5$ is selected from $C_1$-$C_4$-alkyl, which is unsubstituted, partially or fully halogenated, or substituted by 1 or 2 identical or different substituents $R^x$, wherein $R^x$ is selected from CN and $C(O)NH_2$, and $C_3$-$C_6$-cycloalkyl, which is unsubstituted or substituted by 1, 2 or 3 identical or different substituents $R^y$, wherein $R^y$ is selected from halogen, CN and $C(O)NH_2$.

In an even more preferred embodiment, $R^4$ is selected from $C_1$-$C_4$-alkyl, which is unsubstituted, partially or fully halogenated, or substituted by 1 or 2 identical or different substituents $R^x$, wherein $R^x$ is selected from CN and $C(O)NH_2$, and $C_3$-$C_6$-cycloalkyl, which is unsubstituted or substituted by 1, 2 or 3 identical or different substituents $R^y$, wherein $R^y$ is selected from halogen, CN and $C(O)NH_2$; and $R^5$ is selected from $C_1$-$C_2$-alkyl, which is unsubstituted, partially or fully halogenated, or substituted by 1 or 2 identical or different substituents $R^x$, wherein $R^x$ is selected from CN and $C(O)NH_2$, and $C_3$-$C_4$-cycloalkyl, which is unsubstituted or substituted by 1, 2 or 3 identical or different substituents $R^y$, wherein $R^y$ is selected from halogen, CN and $C(O)NH_2$.

It is particularly preferred that $R^4$ and $R^5$ are different from each other. For example, $R^5$ may be $C_1$-$C_2$-alkyl, which is unsubstituted, or $C_3$-$C_4$-cycloalkyl, which is unsubstituted, while $R^4$ may be $C_1$-$C_4$-alkyl, which is unsubstituted, or partially or fully halogenated, or substituted with 1 or 2 identical or different substituents $R^x$ selected from CN and $C(O)NH_2$, or may be $C_3$-$C_6$-cycloalkyl, which is preferably substituted with 1, 2 or 3 identical or different substituents $R^y$ selected from halogen, CN and $C(O)NH_2$.

Most preferably, $R^5$ is $CH_3$, while $R^4$ is $C_1$-$C_4$-alkyl, $C_1$-$C_2$-haloalkyl, or $C_3$-cycloalkyl, wherein the cycloalkyl group is preferably substituted with one substituent selected from CN and $C(O)NH_2$. Suitable combinations of $R^5$ and $R^4$ may thus e.g. be $CH_3$/i-Pr or $CH_3$/1-CN-c$C_3H_4$.

In another preferred embodiment of the invention, $R^4$ and $R^5$ together with the carbon atom to which they are attached form a 3- to 12-membered non-aromatic carbocycle, which is unsubstituted or partially or fully substituted by $R^j$.

In a more preferred embodiment, $R^4$ and $R^5$ together with the carbon atom to which they are attached form a 3- to 12-membered non-aromatic, saturated carbocycle, which is unsubstituted or partially or fully substituted by $R^j$, wherein $R^j$ is selected from halogen, CN and $C(O)NH_2$.

In an even more preferred embodiment, $R^4$ and $R^5$ together with the carbon atom to which they are attached form a 3- to 6-membered non-aromatic, saturated carbocycle, which is unsubstituted or partially or fully substituted by $R^j$, wherein $R^j$ is selected from halogen, CN and $C(O)NH_2$.

It is particularly preferred according to this embodiment of the present invention that $R^4$ and $R^5$ together with the carbon atom to which they are attached form a 6-membered carbocycle, which is partially or fully halogenated, preferably fluorinated. Thus, $R^4$ and $R^5$ may together represent e.g. —$CH_2CH_2CF_2CH_2CH_2$—.

For the compounds of the present invention, in particular for compounds IV and V, it is particularly preferred that $R^1$ is CN or $C(Y)OR^c$,
wherein Y is O, and $R^c$ is $C_1$-$C_4$-alkyl or benzyl;

$R^2$ is $C_1$-$C_4$-alkyl, which group is unsubstituted, or partially or fully halogenated, preferably $CH_3$, or halomethyl; $CH_3$ is particularly preferred;

$R^3$ is H;

$R^4$ is selected from $C_1$-$C_4$-alkyl, which group is unsubstituted, partially or fully halogenated, and $C_3$-$C_6$-cycloalkyl, which group is unsubstituted or substituted by one or more identical or different substituents $R^y$, wherein $R^y$ is selected from halogen and CN; and $R^5$ is selected from $C_1$-$C_4$-alkyl, which group is unsubstituted, partially or fully halogenated, and $C_3$-$C_6$-cycloalkyl, which group is unsubstituted or substituted by one or more identical or different substituents $R^y$, wherein $R^y$ is selected from halogen and CN.

For the compounds of the present invention, in particular for compounds IV and V, it is particularly preferred that $R^1$ is $C(O)OR^c$, wherein $R^c$ is $C_1$-$C_4$-alkyl or benzyl;

$R^2$ is $CH_3$ or fluoromethyl; $CH_3$ is particularly preferred;

$R^3$ is H;

$R^4$ is selected from $C_1$-$C_4$-alkyl, which group is unsubstituted or partially halogenated, and $R^5$ is selected from $C_1$-$C_4$-alkyl, preferably $CH_3$.

It is even more preferred that $R^1$ is $C(O)OCH_2CH_3$; $R^2$ is $CH_3$; $R^3$ is H; $R^4$ is $CH(CH_3)_2$; and $R^5$ is $CH_3$.

Furthermore, the following combinations of substituents are preferred in the compounds of formula IV and V, and the other compounds of the process of the present invention, if present.

Table 1 Combination, in which $R^1$ is H, $R^2$ is $CH_3$, $R^3$ is H and the combination of $R^4$ and $R^5$ corresponds in each case to one row of Table A Table 2 Combination, in which $R^1$ is F, $R^2$ is $CH_3$, $R^3$ is H and the combination of $R^4$ and $R^5$ corresponds in each case to one row of Table A Table 3 Combination, in which $R^1$ is $CH_3$, $R^2$ is $CH_3$, $R^3$ is H and the combination of $R^4$ and $R^5$ corresponds in each case to one row of Table A Table 4 Combination, in which $R^1$ is $C_6H_5$, $R^2$ is $CH_3$, $R^3$ is H and the combination of $R^4$ and $R^5$ corresponds in each case to one row of Table A Table 5 Combination, in which $R^1$ is $C(O)OCH_3$, $R^2$ is $CH_3$, $R^3$ is H and the combination of $R^4$ and $R^5$ corresponds in each case to one row of Table A Table 6 Combination, in which $R^1$ is $C(O)OCH_2CH_3$, $R^2$ is $CH_3$, $R^3$ is H and the combination of $R^4$ and $R^5$ corresponds in each case to one row of Table A Table 7 Combination, in which $R^1$ is $C(O)OC(CH_3)_3$, $R^2$ is $CH_3$, $R^3$ is H and the combination of $R^4$ and $R^5$ corresponds in each case to one row of Table A Table 8 Combination, in which $R^1$ is $C(O)OCH_2C_6H_5$, $R^2$ is $CH_3$, $R^3$ is H and the combination of $R^4$ and $R^5$ corresponds in each case to one row of Table A Table 9 Combination, in which $R^1$ is CN, $R^2$ is $CH_3$, $R^3$ is H and the combination of $R^4$ and $R^5$ corresponds in each case to one row of Table A Table 10 Combination, in which $R^1$ is H, $R^2$ is $CFH_2$, $R^3$ is H and the combination of $R^4$ and $R^5$ corresponds in each case to one row of Table A Table 11 Combination, in which $R^1$ is F, $R^2$ is $CFH_2$, $R^3$ is H and the combination of $R^4$ and $R^5$ corresponds in each case to one row of Table A Table 12 Combination, in which $R^1$ is $CH_3$, $R^2$ is $CFH_2$, $R^3$ is H and the combination of $R^4$ and $R^5$ corresponds in each case to one row of Table A Table 13 Combination, in which $R^1$ is $C_6H_5$, $R^2$ is $CFH_2$, $R^3$ is H and the combination of $R^4$ and $R^5$ corresponds in each case to one row of Table A Table 14 Combination, in which $R^1$ is $C(O)OCH_3$, $R^2$ is $CFH_2$, $R^3$ is H and the combination of $R^4$ and $R^5$ corresponds in each case to one row of Table A Table 15 Combination, in which $R^1$ is $C(O)OCH_2CH_3$, $R^2$ is $CFH_2$, $R^3$ is H and the combination of $R^4$ and $R^5$ corresponds in each case to one row of Table A Table 16 Combination, in which $R^1$ is $C(O)OC(CH_3)_3$, $R^2$ is $CFH_2$, $R^3$ is H and the combination of $R^4$ and $R^5$ corresponds in each case to one row of Table A Table 17 Combination, in which $R^1$ is $C(O)OCH_2C_6H_5$, $R^2$ is $CFH_2$, $R^3$ is H and the combination of $R^4$ and $R^5$ corresponds in each case to one row of Table A Table 18 Combination, in which $R^1$ is CN, $R^2$ is $CFH_2$, $R^3$ is H and the combination of $R^4$ and $R^5$ corresponds in each case to one row of Table A Table 19 Combination, in which $R^1$ is H, $R^2$ is $CClH_2$, $R^3$ is H and the combination of $R^4$ and $R^5$ corresponds in each case to one row of Table A Table 20 Combination, in which $R^1$ is F, $R^2$ is $CClH_2$, $R^3$ is H and the combination of $R^4$ and $R^5$ corresponds in each case to one row of Table A Table 21 Combination, in which $R^1$ is $CH_3$, $R^2$ is $CClH_2$, $R^3$ is H and the combination of $R^4$ and $R^5$ corresponds in each case to one row of Table A Table 22 Combination, in which $R^1$ is $C_6H_5$, $R^2$ is $CClH_2$, $R^3$ is H and the combination of $R^4$ and $R^5$ corresponds in each case to one row of Table A Table 23 Combination, in which $R^1$ is $C(O)OCH_3$, $R^2$ is $CClH_2$, $R^3$ is H and the combination of $R^4$ and $R^5$ corresponds in each case to one row of Table A Table 24 Combination, in which $R^1$ is $C(O)OCH_2CH_3$, $R^2$ is $CClH_2$, $R^3$ is H and the combination of $R^4$ and $R^5$ corresponds in each case to one row of Table A Table 25 Combination, in which $R^1$ is $C(O)OC(CH_3)_3$, $R^2$ is $CClH_2$, $R^3$ is H and the combination of $R^4$ and $R^5$ corresponds in each case to one row of Table A Table 26 Combination, in which $R^1$ is $C(O)OCH_2C_6H_5$, $R^2$ is $CClH_2$, $R^3$ is H and the combination of $R^4$ and $R^5$ corresponds in each case to one row of Table A Table 27 Combination, in which $R^1$ is CN, $R^2$ is $CClH_2$, $R^3$ is H and the combination of $R^4$ and $R^5$ corresponds in each case to one row of Table A Table 28 Combination, in which $R^1$ is H, $R^2$ is $CF_3$, $R^3$ is H and the combination of $R^4$ and $R^5$ corresponds in each case to one row of Table A Table 29 Combination, in which $R^1$ is F, $R^2$ is $CF_3$, $R^3$ is H and the combination of $R^4$ and $R^5$ corresponds in each case to one row of Table A Table 30 Combination, in which $R^1$ is $CH_3$, $R^2$ is $CF_3$, $R^3$ is H and the combination of $R^4$ and $R^5$ corresponds in each case to one row of Table A Table 31 Combination, in which $R^1$ is $C_6H_5$, $R^2$ is $CF_3$, $R^3$ is H and the combination of $R^4$ and $R^5$ corresponds in each case to one row of Table A Table 32 Combination, in which $R^1$ is $C(O)OCH_3$, $R^2$ is $CF_3$, $R^3$ is H and the combination of $R^4$ and $R^5$ corresponds in each case to one row of Table A Table 33 Combination, in which $R^1$ is $C(O)OCH_2CH_3$, $R^2$ is $CF_3$, $R^3$ is H and the combination of $R^4$ and $R^5$ corresponds in each case to one row of Table A Table 34 Combination, in which $R^1$ is $C(O)OC(CH_3)_3$, $R^2$ is $CF_3$, $R^3$ is H and the combination of $R^4$ and $R^5$ corresponds in each case to one row of Table A Table 35 Combination, in which $R^1$ is $C(O)OCH_2C_6H_5$, $R^2$ is $CF_3$, $R^3$ is H and the combination of $R^4$ and $R^5$ corresponds in each case to one row of Table A Table 36 Combination, in which $R^1$ is CN, $R^2$ is $CF_3$, $R^3$ is H and the combination of $R^4$ and $R^5$ corresponds in each case to one row of Table A Table 37 Combination, in which $R^1$ is $CF_3$, $R^2$ is $C(O)NH$-$(3$-$C(O)NHCH_2C_6H_5,4$-$C_1$-$C_6H_3)$, $R^3$ is $C_2F_5$ and the combination of $R^4$ and $R^5$ corresponds in each case to one row of Table A

TABLE A

| No | $R^4$ | $R^5$ |
| --- | --- | --- |
| A-1 | $CH_3$ | $CH_3$ |
| A-2 | $CF_3$ | $CH_3$ |
| A-3 | $CH(CH_3)_2$ | $CH_3$ |
| A-4 | 1-CN-c-$C_3H_4$ | $CH_3$ |
| A-5 | $CHFCH_3$ | $CH_3$ |
| A-6 | $CH_2CH_2CF_2CH_2CH_2$ | |
| A-7 | H | H |

Above combinations A-1 to A-6 of Tables 1 to 9 are preferred embodiments of the invention.

The above preferences in terms of the substituents of the compounds of the invention are to be understood as preferred on their own, but also in combination with the following preferred embodiments regarding the reaction conditions and relevant components of the process of the invention.

As already indicated above, the present invention relates to a catalytic process for preparing pyrazole compounds V comprising the step of cyclizing hydrazone substituted αβ-unsaturated carbonyl compounds IV, i.e. pyrazole precursors IV, by reacting them with hydrogen in a reaction mixture comprising as components (a) a hydrogenation catalyst, (b) an acid selected from Brønsted acids, ammonium salts of Brønsted acids, and Lewis acids, (c) a protic solvent; and optionally (d) an aprotic solvent.

In the above reaction sequences, said reaction step is referred to as step (c).

It is to be understood that the process may further comprise reaction steps (a) and (b) as defined above for the preparation of the pyrazole precursors IV, and reaction steps (d), (e) and (f) for further transformations of the pyrazole compounds V. However, the present invention particularly focuses on the cyclization of the pyrazole precursors IV according to step (c) as defined above to obtain the pyrazole compounds V.

Preferred embodiments regarding the reaction steps (a) to (f), in particular regarding reaction step (c) of the invention are defined in further detail hereinafter.

In general, the reaction steps are performed in reaction vessels customary for such reactions, the reactions being carried out in a continuous, semi-continuous or batchwise manner.

In general, the reaction steps are preferably carried out under atmospheric pressure. However, reaction step (c) may also be carried out under a hydrogen pressure of more than 1 bar (more than 100 kPa), preferably of at least 5 bar, more preferably from 1 to 50 bar, for technical reasons a pressure of from 5 to 20 bar is usually applied.

The temperatures and the duration times of the reactions may be varied in broad ranges, which the person skilled in the art knows from analogous reactions. The temperatures often depend on the reflux temperature of the solvents. Other reactions are preferably performed at room temperature, i.e. at 25° C., or at 0° C. The end of the reaction can be monitored by methods known to a person skilled in the art, e.g. thin layer chromatography or HPLC.

If not otherwise indicated, the molar ratios of the reactants, which are used in the reactions, are in the range of from 0.2:1 to 1:0.2, preferably from 0.5:1 to 1:0.5, more preferably from 0.8:1 to 1:0.8. Preferably, equimolar amounts are used.

If not otherwise indicated, the reactants can in principle be contacted with one another in any desired sequence.

The person skilled in the art knows when the reactants or reagents are moisture sensitive, so that the reaction should be carried out under protective gases such as under a nitrogen atmosphere, and dried solvents should be used.

The person skilled in the art also knows the best work-up of the reaction mixture after the end of the reaction.

The essential reaction step (c) of the process of the present invention is described hereinafter. The preferred embodiments mentioned above and those still to be illustrated below of reaction step (c) of the process of the invention are to be understood as preferred alone or in combination with each other.

In one embodiment (batch process) for the reaction step (c), the pyrazole precursor IV is provided in a reaction mixture comprising as components
  (a) a hydrogenation catalyst;
  (b) an acid selected from Brønsted acids, ammonium salts of Brønsted acids, and Lewis acids;
  (c) a protic solvent; and optionally
  (d) an aprotic solvent;
  and then reacted with hydrogen to give the desired pyrazole compounds V.

In another embodiment (semi-batch process) for the reaction step (c), a reaction mixture is provided comprising as components
  (a) a hydrogenation catalyst;
  (b) an acid selected from Brønsted acids, ammonium salts of Brønsted acids, and Lewis acids;
  (c) a protic solvent; and optionally
  (d) an aprotic solvent;
  reaction mixture is pressurized with hydrogen;
  then dosed a solution of precursor IV in a protic solvent to give the desired pyrazole compounds V.

The dosing rate of the compound IV solution to the reaction mixture depends on the amount of reactants. A slower dosing usually increases the yield and selectivity of the pyrazole V. Dosing time depends on the volume of the solution to be dosed and of the reaction vessel. For practical reasons the dosing is completed in up to 12 hours, preferably up to four hours. After completion of dosing the reaction is completed after another one to two hours stirring.

As used herein, the term "hydrogenation catalyst" covers heterogeneous and homogeneous hydrogenation catalysts, but preferably refers to heterogeneous catalysts. It is known in the art that platinum, palladium, rhodium, and ruthenium form highly active catalysts. Non-precious metal catalysts, such as catalysts based on nickel (such as Raney nickel and Urushibara nickel) are economical alternatives. Preferred hydrogenation catalysts according to the invention are provided further below.

In a preferred embodiment of the invention, the hydrogenation catalyst comprises platinum or palladium. The platinum or palladium may be provided on a carrier, for example on carbon, calcium carbonate, strontium carbonate, barium carbonate, alumina, barium sulphate, kieselguhr, or magnesium silicate. Preferably, the platinum or palladium is provided on carbon.

In a preferred embodiment of the invention, the hydrogenation catalyst is selected from Pd/C, Pt/C, and $PtO_2$.

It has been found that platinum catalysts are particularly advantageous in terms of increasing the yields of the desired pyrazoles V and in terms of the prevention of the formation of the undesired NH-pyrazoles $V^H$.

In a particularly preferred embodiment of the invention, the hydrogenation catalyst is therefore selected from Pt/C and $PtO_2$. It is most preferred in the context of the present invention that the hydrogenation catalyst is Pt/C.

In a preferred embodiment of the invention, the hydrogenation catalyst is present in the reaction mixture in an amount of at least 0.05 mol % based on the molar amount of the pyrazole precursor IV. Preferably, the hydrogenation catalyst is present in an amount of at least 0.1 mol %, more preferably at least 0.3 mol %. It can also be preferred to use at least 0.5 mol %.

In view of the costs of the hydrogenation catalyst, it is advantageous to use rather low amounts of the catalyst. Therefore, an upper limit of 5 mol % of the hydrogenation catalyst based on the molar amount of the pyrazole precursor IV can be preferred. A skilled person is aware however that higher amounts of the hydrogenation catalyst do not negatively affect the hydrogenation reaction.

Suitable amounts may thus be in the range of from 0.05 to 5.0 mol %, preferably from 0.1 to 1.0 mol % or from 0.5 to 1.0 mol % based on the molar amount of the pyrazole precursor IV.

However, in a fixed bed case, also amounts of more than 5.0 mol % may be used.

In one preferred embodiment, the hydrogenation catalyst comprises Pt or Pd, and is present in an amount of at least 0.05 mol % based on the molar amount of the pyrazole precursor IV.

In another preferred embodiment, the hydrogenation catalyst comprises Pt or Pd, and is present in an amount of at least 0.1 mol % based on the molar amount of the pyrazole precursor IV.

In another preferred embodiment, the hydrogenation catalyst comprises Pt or Pd, and is present in an amount of at least 0.5 mol % based on the molar amount of the pyrazole precursor IV.

In one preferred embodiment, the hydrogenation catalyst is $PtO_2$, and is present in an amount of at least 0.05 mol % based on the molar amount of the pyrazole precursor IV.

In another preferred embodiment, the hydrogenation catalyst is $PtO_2$, and is present in an amount of at least 0.1 mol % based on the molar amount of the pyrazole precursor IV.

In another preferred embodiment, the hydrogenation catalyst is $PtO_2$, and is present in an amount of at least 0.5 mol % based on the molar amount of the pyrazole precursor IV.

In one preferred embodiment, the hydrogenation catalyst is Pt/C, and is present in an amount of at least 0.05 mol % based on the molar amount of the pyrazole precursor IV.

In another preferred embodiment, the hydrogenation catalyst is Pt/C, and is present in an amount of at least 0.1 mol % based on the molar amount of the pyrazole precursor IV.

In another preferred embodiment, the hydrogenation catalyst is Pt/C, and is present in an amount of at least 0.5 mol % based on the molar amount of the pyrazole precursor IV.

The acid in the reaction mixture is selected from Brønsted acids, ammonium salts of Brønsted acids, and Lewis acids.

As used herein, the term "Brønsted acid" refers to an acid, which donates a proton in an acid-base reaction. In the context of proton donation, a Brønsted acid HA may be considered as dissociating into A− and H+. The $pK_a$ value defines the strength of the Brønsted acid. The larger the value of $pK_a$, the smaller the extent of dissociation at any given pH (Henderson-Hasselbalch equation) that is, the weaker the acid. Typically, the $pK_a$ values are measured in dilute aqueous solutions at room temperature (i.e. 25° C.). The $pK_a$ values for many acids in water are well known and may be found in available references, such as D. H. Rippin, D. A. Evans, Chem 206 (11/4/05).

In general, a broad range of $pK_a$ values is acceptable for the Brønsted acid acids as used according to the present invention.

In terms of the yields, it is preferred to use a Brønsted acid with a $pK_a$ of less than 6, preferably lass than 5 or less than 4.5. Preferably, the $pK_a$ may be in the range of from −3 to 6, preferably from −3 to 5 or from −3 to 4.5. Rather strong Brønsted acids with a $pK_a$ of from −3 to 3 may advantageously be used. In case of rather strong Brønsted acids with a $pK_a$ of from −3 to 3, it can be preferred to use rather low amounts of the acid as defined further below.

In terms of the prevention of the formation of the NH-pyrazole V*, it can be preferred to use a weaker Brønsted acid with a $pK_a$ in the range of from −0.5 to 6, preferably from −0.5 to 5 or even from more than 3 to 5. In case of weaker Brønsted acids, it can be preferred to use higher amounts of the acid as defined further below.

In one embodiment, the Brønsted acid is selected from $C_1$-$C_4$-alkanoic acids, $C_1$-$C_4$-haloalkanoic acids, aryl carboxylic acids, $C_1$-$C_4$-alkyl sulfonic acids, aryl sulfonic acids, cycloaliphatic sulfonic acids, sulfuric acid, oxyacids of phosphor, and hydrogen halides.

$C_1$-$C_4$-Alkanoic acids, in particular acetic acid and formic acid may at the same time be used as protic solvents in the reaction mixture. In one preferred embodiment, the Brønsted acid is therefore selected from $C_1$-$C_4$-alkanoic acids.

In another preferred embodiment, the Brønsted acid is selected from $C_1$-$C_4$-haloalkanoic acids, aryl carboxylic acids, $C_1$-$C_4$-alkyl sulfonic acids, aryl sulfonic acids, cycloaliphatic sulfonic acids, sulfuric acid, oxyacids of phosphor, and hydrogen halides.

As used herein, the term "$C_1$-$C_4$-alkanoic acids" refers to carboxylic acids $R^A$—$CO_2H$, wherein the group $R^A$ is selected from $C_1$-$C_4$-alkyl. Examples of $C_1$-$C_4$-alkanoic acids are formic acid, acetic acid, propionic acid, and butyric acid. Preferred $C_1$-$C_4$-alkanoic acids, which may also be used as protic solvents, are formic acid and acetic acid, in particular acetic acid (AcOH).

As used herein, the term "$C_1$-$C_4$-haloalkanoic acids" refers to carboxylic acids $R^B$—$CO_2H$, wherein the group $R^B$ is selected from $C_1$-$C_4$-haloalkyl. Preferred are "halogenated acetic acids", i.e. halogenated derivatives of acetic acid, wherein 1, 2, or 3 hydrogen atoms are replaced by identical or different halogens. Preferred halogenated acetic acids include trifluoroacetic acid (TFA), trichloroacetic acid (TCAA), and chloroacetic acid (Cl—AcOH). A preferred halogenated acetic acid is trifluoroacetic acid (TFA).

As used herein, the term "aryl carboxylic acids" generally refers to carboxylic acids $R^C$—$CO_2H$, wherein the group $R^C$ is aryl, wherein the aryl group is unsubstituted or substituted by one or more identical or different substituents selected from halogen, $NO_2$, CN, C(=O)H, C(=O)$CH_3$, $C_1$-$C_4$-alkyl, $C_1$-$C_4$-haloalkyl, and $C_1$-$C_4$-alkoxy. The aryl group itself may be phenyl or naphthyl. Examples of aryl carboxylic acids are benzoic acid, 4-methylbenzoic acid, 2-methylbenzoic acid, 2,4-dimethylbenzoic acid, 4-chlorobenzoic acid, 1-naphthalenecarboxylic acid, 2-naphthalenecarboxylic acid, 2-methyl-1-naphthalenecarboxylic acid, 4-methyl-2-naphthalenecarboxylic acid, 6-methyl-2-naphthalenecarboxylic acid, 1,4-dimethyl-2-naphthalenecarboxylic acid, 1,5-dimethyl-2-naphthalenecarboxylic acid, and 5,6-dimethyl-2-naphthalenecarboxylic acid. A preferred aryl carboxylic acid is benzoic acid ($C_6H_5$—COOH).

As used herein, the term "$C_1$-$C_4$-alkyl sulfonic acids" refers to sulfonic acids $R^D$—$SO_3H$, wherein $R^D$ is $C_1$-$C_4$-alkyl. Examples of $C_1$-$C_4$-alkyl sulfonic acid are methanesulfonic acid (=methylsulfonic acid), ethanesulfonic acid, 1-propanesulfonic acid, 2-propanesulfonic acid, 1-butanesulfonic acid, 2-butanesulfonic acid, and 2-methyl-2-propanesulfonic acid. A preferred $C_1$-$C_4$-alkyl sulfonic acid is methylsulfonic acid (MSA).

As used herein, the term "aryl sulfonic acids" refers to sulfonic acids $R^E$—$SO_3H$, wherein $R^E$ is aryl, wherein the aryl group is unsubstituted or partly or fully substituted by identical or different substituents selected from halogen, $C_1$-$C_4$-alkyl, $C_1$-$C_4$-haloalkyl, and $C_1$-$C_4$-alkoxy. The aryl group itself may be phenyl or naphthyl. Examples of aryl sulfonic acids are benzenesulfonic acid, 4-toluenesulfonic acid, 2-toluenesulfonic acid, 2,4-xylenesulfonic acid, 1-naphthalenesulfonic acid, 2-naphthalenesulfonic acid, 2-methyl-1-naphthalenesulfonic acid, 4-methyl-2-naphthalenesulfonic acid, 6-methyl-2-naphthalenesulfonic acid, 1,4-dimethyl-2-naphthalenesulfonic acid, 1,5-dimethyl-2-naphthalenesulfonic acid, and 5,6-dimethyl-2-naphthalenesulfonic acid. A preferred aryl sulfonic acid is 4-toluenesulfonic acid, i.e. p-toluenesulfonic acid (PTSA).

As used herein, the term "cycloaliphatic sulfonic acids", as used herein, describes sulfonic acids $R^E$—$SO_3H$, wherein the $R^E$ is selected from $C_3$-$C_{10}$-cycloalkyl and $C_3$-$C_{10}$-cycloalkyl-$C_1$-$C_4$-alkyl, wherein $C_3$-$C_{10}$-cycloalkyl in each case is a mono- or bicyclic moiety, which is unsubstituted or substituted by one or more identical or different substituents selected from bromine, chlorine, $C_1$-$C_4$-alkyl, or two of said substituents positioned at the same carbon atom represent the oxygen atom of a carbonyl group. Examples of cycloaliphatic sulfonic acids are cyclohexane sulfonic acid and camphorsulfonic acid.

As used herein, the term "sulfuric acid" refers to $H_2SO_4$.

As used herein, the term "oxyacids of phosphor" encompasses any acid, which has a OH— group or $NH_2$ group bound to phosphor, especially an acid having 1, 2 or 3 OH groups or 1 $NH_2$ group, which are bound to a phosphor atom in the oxidation state III or V. The term "oxyacids of phosphor", as used herein, in particular encompasses the following classes of acids:

Phosphoric acid, its oligomers and its mono- or di-estersorthophosphoric acid ($H_3PO_4$), pyrophosphoric acid, polyphosphoric acids, aryl dihydrogen phosphates, such as phenyl dihydrogen phosphate or 1-naphthyl dihydrogen phosphate, alkyl dihydrogen phosphate, such as butyl dihydrogen phosphate or 2-ethylhexyl dihydrogen phosphate, benzyl dihydrogen phosphate and substituted derivatives thereof, Phosphonic acid, and semiesters thereof,
Phosphinic acids, e.g. Aryl phosphinic acids, such as phenyl phosphinic acid,
Phosphoric amidates, such as diethyl phosphoramidate, dibenzylphospho-ramidate or dibenzyl phosphoramidate.

A preferred oxyacid of phosphor is phosphoric acid ($H_3PO_4$).

As used herein, the term "hydrogen halide" preferably includes HF, HCl, HBr, and HI, and is preferably HCl.

The expression "ammonium salts of Brønsted acids", as used herein, denotes salts obtained by neutralizing Brønsted acids, in particular those mentioned before as preferred, with ammonia or organic amines. In this context organic amines are preferably selected from aromatic amines, such as pyridine or collidine, heterocyclic amines, such as piperidine, 2,2,6,6-tetramethylpiperidine, 2,2,6,6-tetramethylpiperidone or morpholine, aryl amines, such as aniline or 4-methylaniline, secondary and tertiary mixed alkyl-aryl amines, such as N-methyl aniline or N,N-dimethyl aniline, and primary, secondary and tertiary aliphatic amines, such as triethylamine, diethylamine, 1-propylamine or 2-cyclopropyl-2-propylamine, particularly selected from pyridine, collidine, morpholine and trimethylamine, and specifically selected from pyridine and trimethylamine. A preferred ammonium salt of a Brønsted acid is pyridinium methylsulfonate (MSA*pyr).

A Lewis acid is generally understood by a skilled person as an electron pair acceptor.

Preferred Lewis acids for the process according to the invention are selected from halides of metals and metalloids and derivatives thereof. It is to be understood that the term "halides of metals and metalloids" also covers their complexes with Lewis bases, such as $Et_2O$. These complexes (e.g. $BF_3*OEt_2$, wherein $BF_3$ is the "halide of a metal or metalloid" and $Et_2O$ is the Lewis base) typically dissociate under the reaction conditions to provide the Lewis acid. Examples of suitable Lewis acids include $MgF_2$, $BF_3*OEt_2$, $BCl_3$, $AlCl_3$, $AlF_3$, $ZnCl_2$, $FeCl_3$, $PF_5$, $SbF_5$, $TiCl_4$, $BiCl_3$, $GaCl_3$, $SnCl_4$ and $SiCl_4$. In a preferred embodiment the Lewis acid used in the process of the invention is selected from $BF_3*OEt_2$, $FeCl_3$, $TiCl_4$ and $AlCl_3$ with $AlCl_3$ being particularly preferred.

In a preferred embodiment of the invention, the acid is
(b1) a Brønsted acid selected from $C_1$-$C_4$-alkanoic acids, $C_1$-$C_4$-haloalkanoic acids, aryl carboxylic acids, $C_1$-$C_4$-alkyl sulfonic acids, aryl sulfonic acids, cycloaliphatic sulfonic acids, sulfuric acid, oxyacids of phosphor, and hydrogen halides,
(b2) an ammonium salt of a Brønsted acid selected from $C_1$-$C_4$-alkanoic acids, $C_1$-$C_4$-haloalkanoic acids, aryl carboxylic acids, $C_1$-$C_4$-alkyl sulfonic acids, aryl sulfonic acids, cycloaliphatic sulfonic acids, sulfuric acid, oxyacids of phosphor, and hydrogen halides, or
(b3) a Lewis acid selected from halides of metals and metalloids.

In another preferred embodiment of the invention, the acid is
(b1) a Brønsted acid selected from $C_1$-$C_4$-haloalkanoic acids, $C_1$-$C_4$-alkyl sulfonic acids, aryl sulfonic acids, sulfuric acid, oxyacids of phosphor, and hydrogen halides,
(b2) an ammonium salt of a Brønsted acid selected from $C_1$-$C_4$-haloalkanoic acids, $C_1$-$C_4$-alkyl sulfonic acids, aryl sulfonic acids, sulfuric acid, oxyacids of phosphor, and hydrogen halides, or
(b3) a Lewis acid selected from halides of metals and metalloids.

In yet another preferred embodiment of the invention, the acid is
(b1) a Brønsted acid with a $pK_a$ of from −3 to 3,
(b2) an ammonium salt of a Brønsted acid with a $pK_a$ of −3 to 3, or
(b3) a Lewis acid selected from halides of metals and metalloids.

In another preferred embodiment, the acid is
(b1) a Brønsted acid selected from acetic acid (AcOH), trifluoroacetic acid (TFA), trichloroacetic acid (TCAA), chloroacetic acid (Cl—AcOH), methylsulfonic acid (MSA), p-toluenesulfonic acid (PTSA), sulfuric acid ($H_2SO_4$), and phosphoric acid ($H_3PO_4$),
(b2) a pyridinium or trimethylammonium salt of a Brønsted acid selected from acetic acid (AcOH), trifluoroacetic acid (TFA), trichloroacetic acid (TCAA), chloroacetic acid (Cl—AcOH), methylsulfonic acid (MSA), p-toluenesulfonic acid (PTSA), sulfuric acid ($H_2SO_4$), and phosphoric acid ($H_3PO_4$), or
(b3) a Lewis acid selected from $BF_3*OEt_2$, $FeCl_3$, $TiCl_4$, and $AlCl_3$.

In an even more preferred embodiment, the acid is
(b1) a Brønsted acid selected from acetic acid (AcOH), trifluoroacetic acid (TFA), trichloroacetic acid (TCAA), sulfuric acid ($H_2SO_4$), and phosphoric acid ($H_3PO_4$),
(b2) pyridinium methylsulfonate (MSA*pyr), or
(b3) a Lewis acid selected from $BF_3*OEt_2$, $FeCl_3$, $TiCl_4$, and $AlCl_3$.

In an even more preferred embodiment, the acid is
(b1) a Brønsted acid selected from trifluoroacetic acid (TFA), and sulfuric acid ($H_2SO_4$),
(b2) pyridinium methylsulfonate (MSA*pyr), or
(b3) a Lewis acid selected from $BF_3*OEt_2$, $FeCl_3$, $TiCl_4$, and $AlCl_3$.

In a most preferred embodiment, the acid is
(b1) a Brønsted acid selected from trifluoroacetic acid (TFA), and sulfuric acid ($H_2SO_4$),
(b2) pyridinium methylsulfonate (MSA*pyr), or
(b3) a Lewis acid selected from $BF_3*OEt_2$, and $AlCl_3$.

Thus, in one preferred embodiment, the acid is AcOH, TFA, TCAA, Cl—AcOH, $C_6H_5$—COOH,
MSA, PTSA, $H_2SO_4$, or $H_3PO_4$, more preferably AcOH, TFA, TCAA, $H_2SO_4$, or $H_3PO_4$. In a more preferred embodiment, the acid is TFA, TCAA, or $H_2SO_4$. In a most preferred embodiment, the acid is $H_3PO_4$, TFA, or $H_2SO_4$, particularly $H_2SO_4$.

In one particularly preferred embodiment, the acid is $H_3PO_4$.

In one particularly preferred embodiment, the acid is TFA.

In one particularly preferred embodiment, the acid is $H_2SO_4$.

Furthermore, in one preferred embodiment, the acid is a pyridinium or trimethylammonium salt of AcOH, TFA, TCAA, Cl—AcOH, MSA, PTSA, $H_2SO_4$, or $H_3PO_4$.

In one particularly preferred embodiment, the acid is MSA*pyr.

Furthermore, in one preferred embodiment, the acid is $BF_3*OEt_2$, $FeCl_3$, $TiCl_4$, or $AlCl_3$.

In one particularly preferred embodiment, the acid is $BF_3*OEt_2$.

In one particularly preferred embodiment, the acid is $FeCl_3$.

In one particularly preferred embodiment, the acid is $TiCl_4$.

In one particularly preferred embodiment, the acid is $AlCl_3$.

It is to be understood that also combinations of the above defined acids can be used. For example, a combination of a (b1) a Brønsted acid and (b3) a Lewis acid may preferably be used.

The amounts of the acid may be varied depending on the costs and the acidity.

As outlined above, acetic acid, which is rather cheap, may advantageously be used in amounts, so that it can also serve as protic solvent. For example, 10 equivalents or more of acetic acid may then be used in comparison to the pyrazole precursor IV (wherein the equivalents refer to the molar amounts). Other acids may be added to the reaction mixture in stoichiometric amounts or in substochiometric amounts.

In a preferred embodiment of the invention, the acid is present in the reaction mixture in an amount of at least 0.05 mol % based on the molar amount of the pyrazole precursor IV, preferably, the acid is present in the reaction mixture in an amount of at least 0.1 mol %. More preferably, the acid is present in the reaction mixture in an amount of at least 1 mol % based on the molar amount of the pyrazole precursor IV. It is particularly preferred that the acid is present in an amount of at least 5 mol % based on the molar amount of the pyrazole precursor IV. In certain cases, it can also be preferred to use at least 40 mol % of the acid or at least 80 mol % of the acid based on the molar amount of the pyrazole precursor IV.

The preferred amount of the acid depends on the nature of the acid. In one embodiment the acid, which is preferably a Brønsted acid, is used in an amount of about one equivalent, i.e. 0.9 to 1.2 mol equivalents to compound of formula IV. For $H_2SO_4$ about 0.5 mol equivalents, i.e. 0.4 to 0.7 mol equivalents are preferred.

In principal, the acid may also be used in rather high amounts. If the acid also serves as protic solvent, a large excess of the acid will in any case be present. In other cases, amounts up to 200 mol % (i.e. 2 equiv.) can be suitable.

Thus, preferred amounts of the acid may be in the range of from 0.05 to 200 mol %, preferably from 0.1 to 200 mol %, more preferably from 1 to 200 mol % based on the molar amount of the pyrazole precursor IV. A preferred range is from 5 to 200 mol %. For example, 5 to 15 mol %, 15 to 25 mol %, 25 to 35 mol %, 35 to 45 mol %, 45 to 55 mol %, 55 to 65 mol %, 65 to 75 mol %, 75 to 85 mol %, 85 to 95 mol %, or 95 to 105 mol % may be used.

In general, Brønsted acids are typically used in higher amounts than Lewis acids.

Preferably, Brønsted acids are used in an amount of at least 1 mol %, preferably at least 5 mol %, more preferably at least 40 mol %, based on the molar amount of the pyrazole precursor IV. Suitable amounts may vary depending on the strength of the acid.

In case of Brønsted acids with a $pK_a$ of from −3 to 3, it is preferred to use amounts of at least 1 mol %, preferably amounts in the range of from 1 mol % to 100 mol %, more preferably 5 mol % to 100 mol %.

In case of Brønsted acids with a $pK_a$ of from more than 3 to 5, it is preferred to use amounts of at least 5 mol %, preferably at least 40 mol %. It can be suitable to use amounts of from 40 mol % to 200 mol %, or the acid may be used as protic solvent, e.g. in amounts of 10 equivalents or more.

Preferably, ammonium salts of Brønsted acids are used in an amount of at least 5 mol %, preferably at least 40 mol % based on the molar amount of the pyrazole precursor IV. A preferred range is from 40 mol % to 200 mol %.

Preferably, Lewis acids are used in an amount of at least 1 mol %, preferably at least 5 mol % based on the molar amount of the pyrazole precursor IV. A preferred range is from 1 mol % to 200 mol %, preferably from 5 mol % to 100 mol %.

The following combinations B-1 to B-14 of the hydrogenation catalyst (component (a)) and the acid (component (b)) as defined in Table B are preferred according to the present invention.

TABLE B

| No | (a) | (b) |
|---|---|---|
| B-1 | Pt/C | TFA |
| B-2 | Pt/C | $H_2SO_4$ |
| B-3 | Pt/C | MSA*pyr |
| B-4 | Pt/C | $H_3PO_4$ |
| B-5 | Pt/C | $BF_3$*$OEt_2$ |
| B-6 | Pt/C | $TiCl_4$ |
| B-7 | Pt/C | $AlCl_3$ |
| B-8 | $PtO_2$ | TFA |
| B-9 | $PtO_2$ | $H_2SO_4$ |
| B-10 | $PtO_2$ | MSA*pyr |
| B-11 | $PtO_2$ | $H_3PO_4$ |
| B-12 | $PtO_2$ | $BF_3$*$OEt_2$ |
| B-13 | $PtO_2$ | $TiCl_4$ |
| B-14 | $PtO_2$ | $AlCl_3$ |

Especially preferred combinations are combinations B-1 to B-7, with combination B-1, B-2, and B-7 being particularly preferred in terms of the yields and B-1, B-4, and B-7 being particularly preferred in terms of the selectivity of the cyclization reaction.

As used herein, the term "protic solvent" generally includes solvents that have a hydrogen atom bound to an oxygen atom (as in a hydroxyl group) or a nitrogen atom (as in an amine group), so that they can principally donate protons ($H^+$) to reagents.

Preferred protic solvents include $C_1$-$C_4$-alkanols, $C_2$-$C_4$-alkandiols, ether alkanols, water, acetic acid, formic acid, and mixtures thereof.

$C_1$-$C_4$-alkanols generally include methanol, ethanol, propanol, isopropanol, n-butanol, sec-butanol, and tert-butanol. Preferred $C_1$-$C_4$-alkanols include methanol (MeOH), ethanol (EtOH), n-propanol and isopropanol. Preferred are methanol and ethanol. Particularly preferred is ethanol. Another particularly preferred solvent is methanol.

Preferred $C_2$-$C_4$-alkandiols include ethylene glycol or propylene glycol.

Preferred ether alkanols include as diethylene glycol.

In one embodiment, the protic solvent is selected from $C_1$-$C_4$-alkanols, water, acetic acid, formic acid, and mixtures thereof. An exemplary mixture is ethanol/acetic acid.

In one preferred embodiment, the protic solvent is acetic acid.

In another preferred embodiment, the protic solvent is selected from $C_1$-$C_4$-alkanols and mixtures thereof. In a more preferred embodiment, the protic solvent is methanol or ethanol or isopropanol. In a particularly preferred embodiment, the protic solvent is ethanol.

It has surprisingly been found that the use of ethanol as a solvent in the reaction mixture is particularly advantageous in terms of increasing the yields of the desired pyrazoles V and in terms of the prevention of the formation of the undesired NH-pyrazoles $V^H$.

The following combinations C-1 to C-6 of the hydrogenation catalyst (component (a)) and the protic solvent (component (c)) as defined in Table C are preferred according to the present invention.

TABLE C

| No | (a) | (c) |
|---|---|---|
| C-1 | Pt/C | CH(CH$_3$)$_2$OH |
| C-2 | Pt/C | CH$_3$CH$_2$OH |
| C-3 | Pt/C | CH$_3$OH |
| C-4 | PtO$_2$ | CH(CH$_3$)$_2$OH |
| C-5 | PtO$_2$ | CH$_3$CH$_2$OH |
| C-6 | PtO$_2$ | CH$_3$OH |

Especially preferred are combinations C-1 to C-3, with combinations C-2 and C-3 being particularly preferred.

Furthermore, the following combinations D-1 to D-42 of the hydrogenation catalyst (component (a)), the acid (component (b)), and the protic solvent (component (c)) as defined in Table D are preferred according to the present invention.

TABLE D

| No | (a) | (b) | (c) |
|---|---|---|---|
| D-1 | Pt/C | TFA | CH(CH$_3$)$_2$OH |
| D-2 | Pt/C | H$_2$SO$_4$ | CH(CH$_3$)$_2$OH |
| D-3 | Pt/C | MSA*pyr | CH(CH$_3$)$_2$OH |
| D-4 | Pt/C | BF$_3$*OEt$_2$ | CH(CH$_3$)$_2$OH |
| D-5 | Pt/C | H$_3$PO$_4$ | CH(CH$_3$)$_2$OH |
| D-6 | Pt/C | TiCl$_4$ | CH(CH$_3$)$_2$OH |
| D-7 | Pt/C | AlCl$_3$ | CH(CH$_3$)$_2$OH |
| D-8 | Pt/C | TFA | CH$_3$CH$_2$OH |
| D-9 | Pt/C | H$_2$SO$_4$ | CH$_3$CH$_2$OH |
| D-10 | Pt/C | MSA*pyr | CH$_3$CH$_2$OH |
| D-11 | Pt/C | BF$_3$*OEt$_2$ | CH$_3$CH$_2$OH |
| D-12 | Pt/C | H$_3$PO$_4$ | CH$_3$CH$_2$OH |
| D-13 | Pt/C | TiCl$_4$ | CH$_3$CH$_2$OH |
| D-14 | Pt/C | AlCl$_3$ | CH$_3$CH$_2$OH |
| D-15 | Pt/C | TFA | CH$_3$OH |
| D-16 | Pt/C | H$_2$SO$_4$ | CH$_3$OH |
| D-17 | Pt/C | MSA*pyr | CH$_3$OH |
| D-18 | Pt/C | BF$_3$*OEt$_2$ | CH$_3$OH |
| D-19 | Pt/C | H$_3$PO$_4$ | CH$_3$OH |
| D-20 | Pt/C | TiCl$_4$ | CH$_3$OH |
| D-21 | Pt/C | AlCl$_3$ | CH$_3$OH |
| D-22 | PtO$_2$ | TFA | CH(CH$_3$)$_2$OH |
| D-23 | PtO$_2$ | H$_2$SO$_4$ | CH(CH$_3$)$_2$OH |
| D-24 | PtO$_2$ | MSA*pyr | CH(CH$_3$)$_2$OH |
| D-25 | PtO$_2$ | BF$_3$*OEt$_2$ | CH(CH$_3$)$_2$OH |
| D-26 | PtO$_2$ | H$_3$PO$_4$ | CH(CH$_3$)$_2$OH |
| D-27 | PtO$_2$ | TiCl$_4$ | CH(CH$_3$)$_2$OH |
| D-28 | PtO$_2$ | AlCl$_3$ | CH(CH$_3$)$_2$OH |
| D-29 | PtO$_2$ | TFA | CH$_3$CH$_2$OH |
| D-30 | PtO$_2$ | H$_2$SO$_4$ | CH$_3$CH$_2$OH |
| D-31 | PtO$_2$ | MSA*pyr | CH$_3$CH$_2$OH |
| D-32 | PtO$_2$ | BF$_3$*OEt$_2$ | CH$_3$CH$_2$OH |
| D-33 | PtO$_2$ | H$_3$PO$_4$ | CH$_3$CH$_2$OH |
| D-34 | PtO$_2$ | TiCl$_4$ | CH$_3$CH$_2$OH |
| D-35 | PtO$_2$ | AlCl$_3$ | CH$_3$CH$_2$OH |
| D-36 | PtO$_2$ | TFA | CH$_3$OH |
| D-37 | PtO$_2$ | H$_2$SO$_4$ | CH$_3$OH |
| D-38 | PtO$_2$ | MSA*pyr | CH$_3$OH |
| D-39 | PtO$_2$ | BF$_3$*OEt$_2$ | CH$_3$OH |
| D-40 | PtO$_2$ | H$_3$PO$_4$ | CH$_3$OH |
| D-41 | PtO$_2$ | TiCl$_4$ | CH$_3$OH |
| D-42 | PtO$_2$ | AlCl$_3$ | CH$_3$OH |

Especially preferred combinations are combinations D-8 to D-14, with combination D-8, D-9, D-11, and D-14 being particularly preferred. In another embodiment D-9, D-12 and D-16 are particularly preferred.

As used herein, the term "aprotic solvent" refers to solvents that cannot donate protons. The aprotic solvent is only an optional component of the reaction mixture of the invention, and may for example be present as a co-solvent.

In one embodiment, the aprotic solvent is selected from aromatic solvents, alkane solvents, ether solvents, ester solvents, and mixtures thereof.

Preferred aromatic solvents are e.g. benzene, toluene, xylene (ortho-xylene, meta-xylene or para-xylene), mesitylene, chlorobenzene (MCB), 1,2-dichlorobenzene, 1,3-dichlorobenzene, 1,4-dichlorobenzene, or mixtures thereof. More preferred aromatic solvents are selected from toluene, xylene (ortho-xylene, meta-xylene or para-xylene), chlorobenzene, and mixtures thereof. Particularly preferred is toluene as aromatic solvent.

Preferred alkane solvents include aliphatic hydrocarbons such as pentane, hexane, heptane, cyclohexane, petroleum ether, or mixtures thereof, and halogenated hydrocarbons such as methylene chloride, chloroform, or mixtures thereof. A particularly preferred alkane solvent is heptane.

Preferred ether solvents are open-chained and cyclic ethers, in particular diethyl ether, methyltert-butyl-ether (MTBE), 2-methoxy-2-methylbutane, cyclopentylmethylether, 1,4-dioxane, tetrahydrofuran (THF), 2-methyltetrahydrofuran (CH$_3$-THF), or mixtures thereof. Preferred ether solvents are selected from tetrahydrofuran (THF), 2-methyltetrahydrofuran (CH$_3$-THF), methyl-tertbutyl-ether (MTBE), and mixtures thereof. A particularly preferred ether solvent is MTBE.

Preferred ester solvents include carboxylic esters such as ethyl acetate or butyl acetate.

Further preferred aprotic solvents include acetone, acetonitrile and dimethylformamide.

In a preferred embodiment of the invention, the aprotic solvent is selected is selected from toluene (C$_6$H$_5$—CH$_3$), xylene (ortho-xylene, meta-xylene or para-xylene), chlorobenzene (MCB), heptane, tetrahydrofuran (THF), 2-methyltetrahydrofuran (CH$_3$-THF), methyl-tert-butyl-ether (MTBE), 1,4-dioxane, ethyl acetate (EtOAc), butyl acetate, acetone, acetonitrile, and mixtures thereof.

As indicated above, the aprotic solvent is an optional component of the reaction mixture, and may thus be present or not present in the reaction mixture, wherein the pyrazole precursor IV is provided for the cyclization reaction. Typically, the aprotic solvent, if present, is the solvent, wherein the pyrazole precursor has been prepared. If the solvent is not removed after the preparation of the pyrazole precursor, the cyclization reaction can also be performed in the presence of the aprotic solvent, although it is not essential that the aprotic solvent is present in the reaction mixture. However, the presence of a protic solvent is required according to the invention. It is thus to be understood that the preferred reaction mixtures according to combinations D-1 to D-42 as defined above may according to one embodiment further comprise an aprotic solvent as component (d), which may e.g. be C$_6$H$_5$—CH$_3$, MTBE, or EtOAc.

On the other hand, the preferred reaction mixtures not further comprise an aprotic solvent as component (d). The particularly preferred combinations D-1 to D-42 may not further comprise an aprotic solvent as component (d).

As outlined above, the pyrazole precursor IV is provided in a reaction mixture comprising components (a), (b), (c), and optionally (d) as defined above. Suitable amounts of the components (a) and (b) have been defined above. A skilled person knows suitable amounts of the solvent for the reaction.

In order to improve the selectivity of the cyclization reaction in that the formation of the undesired NH-pyrazoles V* is prevented, one strategy is to work at rather low concentrations. This applies in particular if the process is performed batch wise. Other strategies for improving the selectivity include modifying the acid, e.g. using a weaker acid, or dosing of the acid. Furthermore, it can be advantageous to add a water scavenger to the reaction mixture, for example molecular sieves, sodium, magnesium and calcium salts (preferably sodium sulfate, magnesium sulfate, calcium chloride), trimethyl orthoformate, triethyl orthoformate, phosphoryl chloride, phosphorus pentachloride, oleum, acetic anhydride, alkyl acyl chlorides, benzoyl chlorides, sulfuryl chlorides, carbodiimides, aluminum or silicon based resins or oxides.

In a preferred embodiment of the invention, the compound of formula IV is present in the reaction mixture in an amount of at most 50 wt.-%, preferably at most 20 wt.-%, based on the total weight of the reaction mixture.

The preferred concentration of compound IV in the reaction mixture is from 5 to 20 wt.-%. In a more preferred embodiment, the compound of formula IV is therefore present in the reaction mixture in an amount of at most 10 wt.-%, based on the total weight of the reaction mixture.

Preferred amount ranges of the compound of formula IV in the reaction mixture are from 0.1 to 20 wt.-%, preferably 1 to 10 wt.-%, more preferably 1 to 5 wt.-% based on the total weight of the reaction mixture. For example, the compound of formula IV may be present in the reaction mixture in an amount of 5±1 wt.-%. A lower concentration generally favours the formation of the pyrazole V.

In a semi-batch process the compound of formula IV is in a solution dosed into the reaction mixture. The concentration of of IV in the solvent is not critical, an upper limit is given only by the solubility of IV in the solvent, it is usually 20-50 wt-%. By slowly dosing the solution of IV into the reaction mixture the concentration of unreacted IV in the reaction mixture is very low. The final concentration of the pyrazole V in the reaction mixture is usually in the range of 5 to 20 wt. %, preferably 10 to 15 wt-%.

A skilled person is aware that the concentrations may be higher in a continuous or semi-continuous process. In this connection, also concentrations of more than 10 wt.-% or more than 20 wt.-%, e.g. from 20 to 80 wt.-% or from 20 to 50 wt.-%, based on the total weight of the reaction mixture, may be used.

The pyrazole precursor IV being provided in the reaction mixture as defined above is reacted with hydrogen according to the invention, which results in the formation of the pyrazole compounds of formula V via a cyclization reaction.

The hydrogen is typically provided in gaseous form. Suitable reaction vessels for such hydrogenation reactions are known to a skilled person. Further details in this regard are provided further below.

In one embodiment of the invention, the reaction with hydrogen is performed at a temperature of at least −20° C., preferably of at least 0° C.

In a preferred embodiment, the reaction with hydrogen is performed at a temperature of from −20° C. to 40° C., of from 0 to 40° C., e.g. in the range of 5 to 15° C., at room temperature (i.e. 20-25° C.) or at a temperature from 25° C. to 35° C.

In one embodiment of the invention, the hydrogen is provided with a pressure of at least 1 bar (100 kPa).

In a preferred embodiment, the hydrogen is provided with a pressure of at least 5 bar (500 kPa).

A skilled person is aware that the hydrogen pressure depends on the reaction vessels. If the process is performed as a batch process, the hydrogen pressure preferably does not exceed 100 bar (10000 kbar), while in a continuous process, pressures up to 500 bar (50000 kPa) can be suitable. A higher pressure usually increases the selectivity of the reaction, and suppresses the formation of by-products. For technical reasons however, the reaction is preferably run at a pressure of from 5 to 80 bar, particularly from 5 to 20 bar.

In one embodiment of the invention, the process is performed (i) as a batch process, wherein hydrogen is provided with a pressure of 5 to 80 bar (500 to 8000 kPa), preferably 5 to 50 bar (500 to 5000 kPa), particularly from 5 to 20 bar (500 to 2000 kPa), e.g. 10 bar (1000 kPa); or (ii) as a continuous process, wherein hydrogen is provided with a pressure of 5 to 500 bar (500 to 50000 kPa), preferably from 10 to 250 bar (1000 to 25000 kPa), particularly from 50 to 100 bar (5000 to 10000 kPa).

In another embodiment the process is performed as a semi-batch process with a pressure of 5 to 500 bar (500 to 50000 kPa), preferably from 10 to 250 bar (1000 to 25000 kPa), particularly from 5 to 25 bar (5000 to 2500 kPa); e.g. 10 to 20 bar (1000 to 2000 kPa).

If micro flow reactors are used, a preferred pressure range is from 10 to 500 bar (1000 to 50000 kPa), preferably from 100 to 500 bar (10000 to 50000 kPa).

In view of the above, it is emphasized that reaction step (c) of the process of the invention may be operated in batch, semi-batch or continuous mode using a conventional stirred tank reactor. Alternative continuous multiphase catalytic reactors can be also used, where the catalyst can be fixed (trickle bed or packed column technology) or mobile (slurry bubble column, jet/loop reactor or air lift reactor). In this regard, reference is made to E. H. Stitt (Chemical Engineering Journal, 2002, 90, 47-60). New continuous flow reactors can be also employed using a slurry (falling film or corning reactors) as described by M. Irfan et al. (ChemSusChem 2011, 4, 300-316) or a supported catalyst (packed bed, monolith or wall-coated) as described by R. Munirathinam et al. (Adv. Synth. Catal. 2015, 357, 1093-1123).

As already indicated above, the process of the invention may further comprise reaction steps (a) and (b) as defined above for the preparation of the pyrazole precursors IV. These reaction steps of the process of the present invention are described hereinafter.

The preferred embodiments mentioned above and those still to be illustrated below of reaction steps (a) and (b) of the process of the invention are to be understood as preferred alone or in combination with each other and in combination with the preferences regarding process step (c).

In addition to the essential process step (c), the process of the invention in a preferred embodiment further comprises the step (b) of preparing the hydrazone substituted α,β-unsaturated carbonyl compound of formula IV

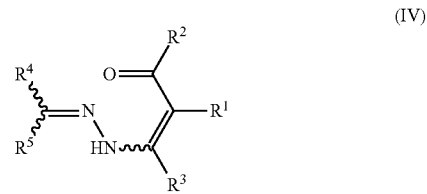

(IV)

by reacting an α,β-unsaturated carbonyl compound of formula III

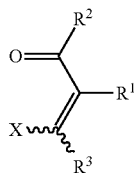

(III)

with a hydrazone compound of formula II

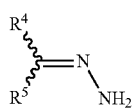

(II)

wherein

X is halogen, OH, $C_1$-$C_{10}$-alkoxy, $C_3$-$C_{10}$-cycloalkoxy, $C_1$-$C_{10}$-alkyl-C(O)O—, $C_1$-$C_{10}$-alkyl-S(O)$_2$O—, $C_1$-$C_{10}$-haloalkyl-S(O)$_2$O—, phenyl-S(O)$_2$O—, tolyl-S(O)$_2$O—, ($C_1$-$C_{10}$-alkyloxy)$_2$P(O)O—, $C_1$-$C_{10}$-alkylthio, $C_3$-$C_{10}$-cycloalkylthio, $C_1$-$C_{10}$-alkyl-C(O)S—, NH$_2$, $C_1$-$C_{10}$-alkylamino, $C_1$-$C_{10}$-dialkylamino, morpholino, N-methylpiperazino, or aza-$C_3$-$C_{10}$-cycloalkyl; and is preferably OCH$_2$CH$_3$;

and $R^1$, $R^2$, $R^3$, $R^4$ and $R^5$ are as defined above.

In certain preferred embodiments X is halogen, $C_1$-$C_4$-alkoxy, $C_1$-$C_4$-dialkylamino, morpholino, N-methylpiperazino, or aza-$C_5$-$C_6$-cycloalkyl.

In one preferred embodiment X is halogen, preferably chlorine.

In another preferred embodiment X is $C_1$-$C_4$-dialkylamino or $C_1$-$C_4$-alkoxy.

In a more preferred embodiment, X is $C_1$-$C_4$-dialkylamino, preferably dimethylamino or diethylamino.

In another more preferred embodiment, X is $C_1$-$C_4$-alkoxy, in particular $C_1$-$C_2$-alkoxy, preferably OCH$_2$CH$_3$.

It is to be understood that the above defined preferences regarding the substituents $R^1$, $R^2$, and $R^3$ also apply in combination with the preferences regarding the substituent X to the compounds of formula III. For example, it is preferred that in the compounds of formula III, $R^1$, $R^2$, and $R^3$ correspond to a combination according to any one of Tables 1 to 9, and X is Cl. Furthermore, it is preferred that in the compounds of formula III, $R^1$, $R^2$, and $R^3$ correspond to a combination according to any one of Tables 1 to 9, and X is OCH$_3$. Furthermore, it is preferred that in the compounds of formula III, $R^1$, $R^2$, and $R^3$ correspond to a combination according to any one of Tables 1 to 9, and X is OCH$_2$CH$_3$. Furthermore, it is preferred that in the compounds of formula III, $R^1$, $R^2$, and $R^3$ correspond to a combination according to any one of Tables 1 to 9, and X is N(CH$_3$)$_2$. Furthermore, it is preferred that in the compounds of formula III, $R^1$, $R^2$, and $R^3$ correspond to a combination according to any one of Tables 1 to 9, and X is N(CH$_2$CH$_3$)$_2$.

The reaction can be performed under reaction conditions known in the art. In particular, the reaction can be carried out by a process, wherein the compound of formula II is reacted with a compound of formula III either in the absence of a solvent or in an organic solvent, wherein a basic catalyst may optionally be present.

Suitable reaction temperatures for the reaction are in the range of from −20° C. to 50° C., preferably from 15° C. to 40° C., more preferably from 20 to 25° C. It is typically preferred that the compounds of formulae II and III are mixed with each other at temperatures below 0° C., preferably about −20° C., and that the mixture is then allowed to warm to a reaction temperature defined above.

The overall reaction times may vary in a broad range, e.g. from 1 hour to 1 day, preferably from 3 to 12 hours.

The compound of formula II may be provided as the crude product of step (a), i.e. without performing any purification steps prior to step (b), or as part of the reaction mixture obtained in step (a), to which the compound of formula III may then be added.

The compound of formula III is commercially available or can be prepared by methods known in the art.

Preferably, the compound of formula III is used in amounts in the range of from 0.1 to 10.0 mol, preferably from 0.8 to 1.5 mol, more preferably from 0.9 to 1.3 mol per mol of the compound of formula II.

In principal, the reaction can easily be performed without having to use a catalyst. However, the reaction may also be performed in the presence of a basic catalyst. Preferred basic catalysts include BaO, CaO, MgCO$_3$, CaCO$_3$, Na$_2$CO$_3$, K$_2$CO$_3$ and NEt$_3$. If a basic catalyst is used, amounts in the range of from 0.01 to 2.0 mol, preferably from 1.0 to 2.0 mol, per mol of the compound of formula II are preferred.

If a solvent is present, it is preferred that the solvent is an organic solvent, either an aprotic or a protic solvent or a mixture thereof.

It can be preferred that process step (b) of the invention is performed in an aprotic solvent. Preferred aprotic solvents have already been defined above and include aromatic solvents, alkane solvents, ether solvents, ester solvents, and mixtures thereof, especially toluene, xylene (ortho-xylene, meta-xylene or para-xylene), chlorobenzene (MCB), heptane, tetrahydrofuran (THF), 2-methyltetrahydrofuran (CH$_3$-THF), ethyl acetate, butyl acetate, and mixtures thereof. Particularly preferred aprotic solvents in connection with step (b) of the process of the invention are the ether solvents as defined above, preferably THF, CH$_3$-THF, and MTBE, in particular MTBE, and the aromatic solvents as defined above, in particular toluene.

Alternatively, it can be preferred that the process step (b) of the invention is performed in a protic solvent. Protic solvents have already been defined above. Preferred protic solvents in connection with step (b) of the process of the invention are $C_1$-$C_4$-alkanols, in particular ethanol.

Of course, process step (b) may also be performed in a mixture of a protic solvent and an aprotic solvent, for example in a mixture of an ether solvent or an aromatic solvent and a $C_1$-$C_4$-alkanol, preferably in a mixture of MTBE and ethanol or in a mixture of toluene and ethanol.

Performing step (b) in a protic solvent or in a solvent mixture comprising a protic solvent and an aprotic solvent provides the advantage that a composition is obtained, which can directly be used for the subsequent cyclization reaction according to step (c) of the process of the invention by simply adding components (a) and (b) of the above defined reaction mixture.

On the other hand, if step (b) is performed in an aprotic solvent, it is required to add components (a), (b), and (c) of the above defined reaction mixture before performing the cyclization reaction. In certain situation, it can then be preferred to perform a solvent swap, i.e. to replace the aprotic solvent by the protic solvent.

In any case, it is preferred that the pyrazole precursor IV as obtained after step (b) of the process of the invention is not purified before the subsequent cyclization reaction.

Thus, in a preferred embodiment, the step of preparing the pyrazole compound of formula V and the step of preparing the compound of formula IV are performed in a one-pot procedure, wherein the compound of formula IV is subjected to the cyclization reaction without previous purification.

Depending on the solvent, wherein step (b) is performed, the following embodiments are preferred for step (c) of the process of the invention, if performed separately or if performed in a one-pot procedure. It is preferred that (i) if the step of preparing the compound of formula IV is performed in a protic solvent or in a solvent mixture comprising a protic solvent and an aprotic solvent, the step of preparing the pyrazole compound of formula V is performed in the same solvent or solvent mixture as used in the step of preparing the compound of formula IV; or (ii) if the step of preparing the compound of formula IV is performed in an aprotic solvent, the aprotic solvent is replaced by a protic solvent, or a protic solvent is added before the step of preparing the pyrazole compound of formula V.

In connection with option (i), it can of course also be preferred that an additional amount of the protic solvent is added, in order to increase the amount of the protic solvent. It is preferred, however, that no other solvent is added than the solvent(s) already used for the preparation of the compound of formula IV.

In connection with option (ii), the option of performing a solvent swap can be preferred, wherein at least 90 wt.-%, preferably at least 99 wt.-% of the aprotic solvent are removed and a protic solvent is added to replace the removed aprotic solvent. For example, a solvent swap may be performed, wherein an ether solvent is replaced by a $C_1$-$C_4$-alkanol, or preferably MTBE is replaced by ethanol.

Step (a) of the process of the invention covers the preparation of the hydrazone compounds of formula II, wherein hydrazine monohydrate or a solution of hydrazine, is reacted with a compound of formula I either in the absence of a solvent or in an aqueous or organic solvent, wherein a basic or an acidic catalyst may optionally be present.

In a preferred embodiment the reaction is conducted in the absence of a solvent.

In a preferred embodiment the reaction is conducted in the absence of a catalyst.

Suitable reaction temperatures for the reaction are in the range of from 0° C. to 80° C., preferably from 15° C. to 50° C., more preferably from 20 to 25° C. In certain situations, it can be preferred to start at a lower temperature of from 20 to 25° C. for about 1 hour and then heat the reaction mixture to a higher temperature of from 50 to 80° C. In other situations, it can be preferred to start at a medium temperature of from 30 to 50° C. for about 1 hour and then stir the reaction mixture at a temperature of from 20 to 25° C.

The overall reaction times may vary in a broad range, e.g. from 1 hour to 3 days. It is therefore preferred that the reaction is monitored by analytical methods and stopped after complete conversion of the compound of formula I into formula II.

The compound of formula I is commercially available or can be prepared by methods known in the art.

As already indicated above, hydrazine is preferably provided in the form of the monohydrate or in the form of a solution of said monohydrate in water. Preferred concentrations for aqueous hydrazine monohydrate solutions are in the range of 45 to 100% by weight, preferably 60 to 100% by weight, e.g., 80 to 100% or 70 to 90% by weight of hydrazine monohydrate based on the total weight of the solution. Preferably, hydrazine is used as 100% hydrazine monohydrate or as an aqueous solution of hydrazine monohydrate with a concentration of about 80 wt.-% of hydrazine monohydrate based on the total weight of the solution.

Preferably, hydrazine is used at least in stoichiometric amounts. Preferably, hydrazine is used in amounts in the range of from 1.0 to 10.0 mol, preferably from 1.0 to 2.0 mol, more preferably from 1.0 to 1.5 mol, per mol of the compound of formula I.

For practical reasons, it is preferred that the compound of formula I is added to hydrazine monohydrate or a solution thereof and not vice versa, so that it is avoided that an excess of the compound of formula I compared to hydrazine is present in the reaction mixture upon mixing the two components.

If a solvent is present, it is preferred that the solvent is an organic solvent, either an aprotic or a protic solvent or a mixture thereof. Suitable aprotic solvents include aromatic solvents, ethers, or mixtures thereof. Preferred aromatic solvents are e.g. benzene, toluene, xylene (ortho-xylene, meta-xylene or para-xylene), mesitylene, chlorobenzene, 1,2-dichlorobenzene, 1,3-dichlorobenzene, 1,4-dichlorobenzene, or mixtures thereof. Preferred ethers are open-chained and cyclic ethers, in particular diethyl ether, methyl-tert-butyl-ether (MTBE), 2-methoxy-2-methylbutane, cyclopentylmethylether, 1,4-dioxane, tetrahydrofuran, 2-methyltetrahydrofuran, or mixtures thereof. Protic solvents are typically preferred as solvents. Suitable protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Particularly preferred are $C_1$-$C_4$-alkanols, e.g. methanol, ethanol, isopropanol, butanol, or mixtures thereof, in particular ethanol.

The reaction may also be performed in the presence of an acidic or basic catalyst. Preferred acid catalysts include HCl in $H_2O$, HCl in MeOH, HCl in dioxane; $H_2SO_4$, $H_3PO_4$ and salts of $H_2SO_4$ and $H_3PO_4$; aromatic sulfonic acids such as toluene sulfonic acid; alkylsulfonic acids, such as methyl sulfonic acid; aromatic carboxylic acids such as benzoic acid; alkylcarboxylic acids such as acetic acid; salts of rare earth metals; and Lewis acids such as $BF_3$, $BF_3 \times OEt_2$, $BF_3 \times SMe_2$, $TiCl_4$, $Ti(OiPr)_4$. A preferred acid catalyst is acetic acid. Preferred basic catalysts include BaO, CaO, $MgCO_3$, $CaCO_3$, $Na_2CO_3$, $K_2CO_3$ and $NEt_3$. A preferred basic catalyst is BaO.

The acidic or basic catalyst is preferably used in amounts in the range of from 0.001 to 10 mol, preferably from 0.01 to 0.5 mol, more preferably from 0.02 to 0.3 mol, per mol of the compound of formula I. For acidic catalysts, amounts in the range of from 0.05 to 0.2 mol per mol of the compound of formula I can be preferred. For basic catalysts, amounts in the range of from 0.15 to 0.25 or from 0.2 to 0.3 mol per mol of the compound of formula I can be preferred.

In a preferred embodiment, the compounds of formula II are not purified before the preparation of the compounds of formula IV according to step (b) of the process of the invention.

Thus, in a preferred embodiment, the step of preparing the pyrazole precursors IV and the step of preparing the compound of formula II are performed in a one-pot procedure, wherein the compound of formula II is used for reaction step (b) without previous purification.

In a particularly preferred embodiment, process steps (a), (b), and (c) are performed as a one-pot procedure.

The process of the invention may further comprise reaction steps (d), (e) and (f) for further transformations of the pyrazole compounds V, which are obtained according to step (c) of the process of the invention.

The reaction conditions for step (d) of the process of the invention are as follows.

In step (d), a compound of formula Va or Vb is converted into a compound of formula Vc. Typically, said reaction may be understood as a hydrolysis reaction because an ester or a nitrile is hydrolyzed to give the free acid. However, other conversion reactions of esters or nitriles into the free acids, such as the conversion of tert-butyl esters into the free acids by the addition of trifluoroacetic acid, are also covered by the invention.

If the reaction is a according to step (d) is a hydrolysis reaction, the reaction may be carried out by a process, wherein the compound of formula Va or Vb is reacted with water e.g. in the presence of a base or in the presence of an acid, or by a process, wherein the compound of formula Va or Vb is reacted with a water soluble base, preferably an oxo-base, in an aqueous solvent, or by a process, wherein the compound of formula Va or Vb is reacted with a hydroxide in a protic aqueous or organic solvent. Such hydrolysis reactions can be performed according to procedures known in the art.

It is preferred according to the present invention that step (d) is performed by dissolving a compound of formula Va in a protic solvent, either an aqueous solvent such as water or in a protic organic solvent, a such as a $C_1$-$C_4$-alkanol, e.g. methanol, ethanol or isopropanol, and adding a hydroxide.

Suitable hydroxides include alkali metal hydroxides such as lithium, sodium or potassium hydroxide, and mixtures thereof. Sodium hydroxide is particularly preferred.

It is preferred that sodium hydroxide is used in amounts of from 1 to 10 mol, preferably from 2.0 to 6.0 mol, e.g. 2.0 to 3.0 mol or 5.0 to 6.0 mol, per mol of the compound of formula Va.

Suitable reaction temperatures may vary from 20 to 100° C., e.g. from 20 to 25° C. or from 50 to 100° C.

The reaction times may vary from 1 hour to 2 days, e.g. from 1 to 3 hours or from 12 hours to 24 hours or from 1 to 2 days.

The conversion of compounds of formula Va into compounds of formula Vc can be enhanced, and complete conversion can more easily be ensured, if the alcohol, which is formed upon hydrolysis of the compounds of formula Va, is removed from the reaction mixture, e.g. by distillation.

The conversions of compounds of formula Vb into compounds of formula Vc is advantageously performed in an acidic medium, preferably in the presence of $H_2SO_4$ or in the presence of HCl in MeOH. As intermediate compounds, iminoester compounds are formed, which are then hydrolysed to the desired acids of formula Vc.

The resulting compounds of formula Vc can be purified by methods known in the art, e.g. by crystallization under suitable pH conditions.

The reaction conditions for steps (e) and (f) of the process are as follows.

In step (e), the compound of formula Vc is activated by converting it into the activated acid derivative of formula VI.

Suitable peptide coupling reagents, which may be used for introducing the leaving group $X^1$ of the compounds of formula VI starting from compounds of formula V, are described by Han et al. in Tetrahedron 60 (2004) 2447-2467. In this regard, N,N'-bis(2-oxo-3-oxazolidinyl)-phosphinic chloride (BOP—Cl) and O-(7-azabenzotriazol-1-yl)-1,1,3,3-tetramethyluronium hexafluorophosphate (HATU) are preferred according to the present invention.

In addition to the conversion of the compounds of formula Vc into activated acid derivatives of formula VI by means of these peptide coupling reagents, it has also been described in the art how leaving groups such as halogen, $N_3$, p-nitrophenoxy and pentafluorophenoxy can be introduced into the compounds of formula Vc to give the corresponding compounds of formula VI. In this regard, reference is made to WO 2009/027393 and WO 2010/034737.

The compound of formula VI may either be directly converted into a compound of formula VIII or isolated. It is preferred, however, that the compound of formula VI is directly converted into the compound of formula VIII.

The conversion of compounds of formula VI into compounds of formula VIII by reacting the compounds of formula VI with compounds of formula VIII has already been described in WO 2009/027393 and WO 2010/034737.

It is to be understood that the essential reaction step of the process of the invention is reaction step (c), i.e. the preparation of the pyrazole compounds V starting from the pyrazole precursors IV.

In this connection, and in particular in connection with a continuous process, it can also be preferred to prepare certain compositions, which can be used as starting materials for the preparation of the above defined reaction mixture comprising the pyrazole precursor IV, which is then subjected to the hydrogen induced cyclization reaction in step (c) of the process of the invention.

This is illustrated in FIG. 1, which shows a preferred scheme for performing reaction step (c) of the process of the invention by providing a first composition (referred to as "IV+EtOH (c)") comprising the pyrazole precursor IV and ethanol, i.e. component (c) of the desired reaction mixture, and a second composition (referred to as "(b)+EtOH (c)") comprising an acid selected from Brønsted acids, ammonium salts of Brønsted acids, and Lewis acids, i.e. component (b) of the desired reaction mixture, and ethanol, i.e. component (c) of the desired reaction mixture, and combining said compositions with Pt/C as hydrogenation catalyst, i.e. component (a), in a suitable reaction vessel to form the desired reaction mixture for the cyclization reaction of the pyrazole precursor IV, and subjecting said reaction mixture comprising the pyrazole precursor IV to hydrogen at a pressure of 10 to 50 bar at a temperature of from 0 to 40° C., to provide a product mixture comprising the pyrazole V, the acid (b) and ethanol (c), whereby the product mixture has already been separated from the hydrogenation catalyst (a).

It is to be understood, however, that the components (a), (b), (c), and optionally (d) as well as the compound IV, can be mixed with one another in any desired sequence, and may be provided either alone or in the form of a composition as defined hereinafter.

In view of the preferred substituent meanings of the compounds of formula IV and V according to the invention as defined above as well as the preferred components of the reaction mixture, wherein the compounds of formula IV are provided for the cyclization reaction, the following compositions are of particular relevance for the process of the present invention.

In one embodiment, the present invention relates to a composition comprising
(1) a compound of formula IV

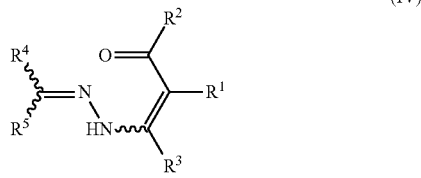

wherein
$R^1$ is $C(O)OCH_2CH_3$; $R^2$ is $CH_3$; $R^3$ is H; $R^4$ is $CH(CH_3)_2$; and $R^5$ is $CH_3$, being compound IV.1, and
(2) at least one component selected from
(a) a hydrogenation catalyst comprising palladium or platinum,
(b) an acid selected from Brønsted acids, ammonium salts of Brønsted acids, and Lewis acids, and
(c) ethanol.

In one preferred embodiment, the present invention relates to a composition A comprising
(1) compound IV.1, and
(2)(a) a hydrogenation catalyst comprising palladium or platinum.

Preferably, the hydrogenation catalyst is Pt/C, or $PtO_2$.

In one particularly preferred embodiment, the hydrogenation catalyst is Pt/C.

This composition may be combined with components (b) and (c) of the reaction mixture as defined above to perform the cyclization reaction in the presence of hydrogen according to step (c) of the process of the invention.

In another preferred embodiment, the present invention relates to a composition B comprising
(1) compound IV.1, and
(2)(b) an acid selected from Brønsted acids, ammonium salts of Brønsted acids, and Lewis acids.

Preferred acids have been defined above.

In a preferred embodiment, the acid is
(b1) a Brønsted acid selected from trifluoroacetic acid (TFA), phosphoric acid ($H_3PO_4$) and sulfuric acid ($H_2SO_4$),
(b2) pyridinium methylsulfonate (MSA*pyr), or
(b3) a Lewis acid selected from $BF_3$*$OEt_2$, $FeCl_3$, $TiCl_4$, and $AlCl_3$.

In one preferred embodiment, the acid is TFA.
In one preferred embodiment, the acid is $H_2SO_4$.
In one preferred embodiment, the acid is MSA*pyr.
In one preferred embodiment, the acid is $BF_3$*$OEt_2$.
In one preferred embodiment, the acid is $FeCl_3$.
In one preferred embodiment, the acid is $TiCl_4$.
In one preferred embodiment, the acid is $AlCl_3$.

This composition may be combined with components (a) and (c) of the reaction mixture as defined above to perform the cyclization reaction in the presence of hydrogen according to step (c) of the process of the invention.

In another preferred embodiment, the present invention relates to a composition C comprising
(1) compound IV.1, and
(2)(c) ethanol.

This composition may be combined with components (a) and (b) of the reaction mixture as defined above to perform the cyclization reaction in the presence of hydrogen according to step (c) of the process of the invention.

It is emphasized that the above composition C is particularly advantageous for the purpose of the present invention, not only because ethanol is a particularly preferred solvent for reaction step (c) of the invention, but also because the reaction mixture, wherein the compound of formula IV is provided, is preferably prepared by mixing composition C (comprising the pyrazole precursor IV and component (c)) with component (b), optionally provided in an additional amount of solvent, and then adding the hydrogenation catalyst (a). In this regard, reference is again made to FIG. 1.

In another preferred embodiment, the present invention relates to a composition D comprising
(1) compound IV.1, and
(2)(c) a $C_1$-$C_4$-alcohol or mixtures thereof, preferably MeOH or EtOH, particularly MeOH.

This composition may be combined with, i.e. slowly dosed to the reaction mixture which comprises components (a), (b) and (c) to perform the cyclization reaction in the presence of hydrogen according to step (c) of the process of the invention.

Particularly for use with composition D the reaction mixture comprises
(2)(a) a hydrogenation catalyst comprising palladium or platinum, preferably Pt/C.
(2)(b) an acid selected from Brønsted acids, ammonium salts of Brønsted acids, and Lewis acids preferably selected from the above list of acids, particularly from $H_2SO_4$ and $H_3PO_4$; and
(2)(c) a $C_1$-$C_4$-alcohol or mixtures thereof, preferably MeOH or EtOH, particularly MeOH.

It is emphasized that the above composition D is particularly advantageous for the purpose of the present invention, not only because methanol is a particularly preferred solvent for the semi-batch process reaction step (c) of the invention, but also because the reaction mixture, to which the solution of compound of formula IV is dosed to, allows a highly selective reaction of compound IV to the pyrazole V.

It is to be understood that the above defined compositions may also comprise combinations of components (a), (b), and (c).

In one preferred embodiment, the present invention therefore relates to a composition comprising
(1) compound IV.1, and
(2) (a) a hydrogenation catalyst comprising palladium or platinum, and
(b) an acid selected from Brønsted acids, ammonium salts of Brønsted acids, and Lewis acids; or
(2) (a) a hydrogenation catalyst comprising palladium or platinum, and
(c) ethanol; or
(2) (b) an acid selected from Brønsted acids, ammonium salts of Brønsted acids, and Lewis acids, and
(c) ethanol.

In another preferred embodiment, the present invention relates to a composition comprising
(1) compound IV.1, and
(2) (a) a hydrogenation catalyst comprising palladium or platinum,
(b) an acid selected from Brønsted acids, ammonium salts of Brønsted acids, and Lewis acids, and
(c) ethanol.

EXAMPLES

I Characterization/Detection

The detection of the compounds can be done by coupled High Performance Liquid Chromatography (HPLC). The following method has been used:

Agilent XDB-C18, 4.6×50 mm, 1.8 µm; mobile phase: A: water+(0.1% $H_3PO_4$); B: acetonitrile (MeCN)+(0.1% $H_3PO_4$); 0-10 min: 5% A, 95% B; 10-10.1 min: 95% A, 5% B; flow: 1.2 mL/min in 10.1 min at 60° C.; UV detector 210 nm.

II Screenings

The following reaction is performed in all screening experiments.

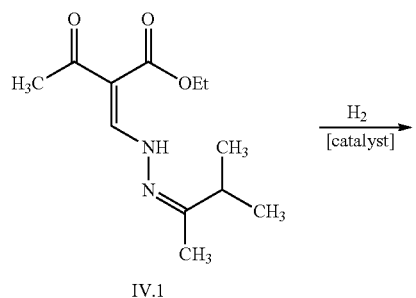

All screening experiments were run in a hastelloy pressure vessel.

Analytics were run using HPLC and all results are presented in area % (=proportion of the area of a specific HPLC peak to the total area of all peaks in percent). Conversion was measured by determining the area % of the starting material, compound IV.1. Furthermore, the area % values of both, the pyrazole V.1 and the corresponding NH-pyrazole $V^H.1$, are in each case determined. The retention times are as follows:

IV.1 (1,4-adduct): 6.3 min  V.1 (pyrazole): 6.1 min  $V^H.1$ (NH-pyrazole): 3.2 min

Example 1: Screening Experiments

Compound IV.1, ethyl 2-[[2-(2,2-dimethyl-1-methyl-ethylidene)hydrazino]methylene]-3-oxo-butanoate (5 g, 0.02 mol), was dissolved in 95 g EtOH. To the solution was first added Pt/C (0.7 g) followed by acid ($H_2SO_4$, 0.5 equiv, 0.9 g). The reaction vessel was pressurized with hydrogen to 10 bar and heated to 30° C. The reaction mixture was stirred for 2 hours. Following the reaction, a sample was taken and the conversion was measured by HPLC. Furthermore, the area % values of the pyrazole V.1, ethyl 1-(2,2-dimethyl-1-methyl-ethyl)-5-methyl-pyrazole-4-carboxylate, and the NH-pyrazole V"0.1 were determined. The results are provided in entry 1 of Table 1A.

Further acids as listed in Table 1A below were tested analogously or according to the modified reaction conditions provided in the respective entry of Table 1A.

TABLE 1A

| No* | Acid | Acid [equiv] | Time [h] | Conversion [%] | Pyrazole V.1 [area %] | NH-pyrazole $V^H.1$ [area %] |
|---|---|---|---|---|---|---|
| 1 | $H_2SO_4$ | 0.5 | 2 | >95 | 74 | 17 |
| 2 | MSA | 1 | 2 | >95 | 51 | 48 |
| 3 | AcOH | 25** | 2 | 64 | 39 | 4 |
| 4 | TFA | 0.5 | 2 | >95 | 85 | 16 |
| 5 | TCAA | 0.5 | 2 | >95 | 67 | 27 |
| 6 | Cl—AcOH | 0.5 | 2 | 33 | 14 | 18 |
| 7 | $H_3PO_4$ | 1 | 3 | 42 | 31 | <1 |
| 8 | $H_3PO_4$ | 1 | 8 | >95 | 90 | 10 |
| 9 | $AlCl_3$ | 0.1 | 3 | >95 | >90 | 2 |
| 10 | $BF_3*OEt_2$ | 0.1 | 3 | 52 | 44 | 2 |
| 11 | MSA*Pyr | 1 | 3 | 45 | 34 | 9 |

*All reactions run with 0.7 g Pt/C in EtOH at 30° C., 10 bar pressure
**EtOH/AcOH = 1:1

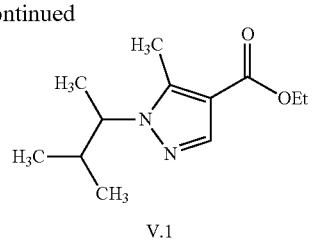

V.1

Furthermore, the influence of the presence of an aprotic solvent was analyzed analogously by using a solvent mixture as defined in Table 1B below and MSA (1 equiv) as the acid.

TABLE 1B

| No* | Solvent mixture | Time [h] | Conversion [%] | Pyrazole V.1 [area %] | NH-pyrazole $V^H.1$ [area %] |
|---|---|---|---|---|---|
| 1 | EtOH/Toluene | 3 | >95 | 53 | 47 |
| 2 | EtOH/EtOAc | 3 | >95 | 62 | 34 |
| 3 | EtOH/MTBE | 3 | >95 | 49 | 45 |

*All reactions run with 0.7 g Pt/C and with 1 equivalent MSA at 30° C., 10 bar pressure

Example 2: Screening Experiment

To a suspension of Pt/C (0.7 g) in 31 g MeOH 1.8 g (0.5 equiv) $H_2SO_4$ were added. The reaction vessel was pressurized with hydrogen to 15 bar and cooled to 10° C. To the reaction mixture was dosed a solution of 9 g ethyl 2-[[2-(2,2-dimethyl-1-methyl-ethylidene)hydrazino]methylene]-3-oxo-butanoate (0.04 mol, compound IV.1) in 20 g MeOH over 240 min using an HPLC pump. The reaction mixture was stirred for an additional hour following the dosing. Then the conversion was measured by HPLC: the area % values of the pyrazole V.1, ethyl 1-(2,2-dimethyl-1-methyl-ethyl)-5-methyl-pyrazole-4-carboxylate, and NH-pyrazole $V^H.1$ were determined. The results are provided in entry 1 of Table 2C.

Further trials were run analogously or according to Example 2; the results are listed in Tables 2C to 2G. All trials run with 0.7 g Pt/C catalyst in same amounts of solvent and compound IV.1.

TABLE 2C

| No* | Solvent | Acid [equiv] | Dosing Time [h] | Post stirring time [h] | Conversion [%] | Pyrazole V.1 [area %] | NH-pyrazole $V^H.1$ [area %] |
|---|---|---|---|---|---|---|---|
| 1 | EtOH | $H_2SO_4$ (0.50) | 4 | 1 | >95 | 93 | 7 |
| 2 | MeOH | $H_2SO_4$ (0.50) | 4 | 1 | >95 | 93 | 7 |
| 3 | EtOH | $H_3PO_4$ (1.0) | 4 | 4 | 72 | 47 | 17 |

*All reactions run at 10° C., 15 bar pressure

TABLE 2D

| No * | Solvent | Temp [° C.] | Pressure [bar] | Dosing/post stirring time [h] | Conversion [%] | Pyrazole V.1 [area %] | NH-pyrazole $V^H.1$ [area %] |
|---|---|---|---|---|---|---|---|
| 4 | EtOH | 10 | 15 | 4/1 | >98 | 80.1 | 19.9 |
| 5 | MeOH | 10 | 15 | 4/1 | >98 | 90.5 | 9.5 |
| 6 | i-propanol | 10 | 15 | 4/1 | >95 | 53.8 | 46.2 |
| 7 | n-butanol | 10 | 15 | 4/1 | >95 | 43.9 | 56.1 |
| 8 | EtOH/Toluene (1:1) | 10 | 15 | 4/1 | >98 | 78.7 | 21.3 |

Concentration of IV.1 in total amount of solvent = 15 wt.-%; Acid = $H_2SO_4$, 0.5 equiv.

TABLE 2E

| No* | Temp [° C.] | Pressure [bar] | Dosing Time [h] | Post stirring time [h] | Conversion [%] | Pyrazole V.1 [area %] | NH-pyrazole $V^H.1$ [area %] |
|---|---|---|---|---|---|---|---|
| 9 | 10 | 5 | 4 | 1 | >98 | 55.9 | 44.1 |
| 10 | 10 | 10 | 4 | 1 | >98 | 70.0 | 30.0 |
| 11 | 10 | 15 | 4 | 1 | >98 | 80.1 | 19.9 |
| 12 | 10 | 20 | 4 | 1 | >98 | 86.0 | 14.0 |

Solvent = EtOH, Concentration of IV.1 in total amount of solvent = 15 wt.-%; Acid = $H_2SO_4$, 0.5 equiv.

TABLE 2F

| No* | Temp [° C.] | Concentration* [%] | Dosing Time [h] | Post stirring time [h] | Conversion [%] | Pyrazole V.1 [area %] | NH-pyrazole $V^H.1$ [area %] |
|---|---|---|---|---|---|---|---|
| 13 | 10 | 10 | 4 | 1 | >98 | 91.3 | 8.7 |
| 14 | 10 | 15 | 4 | 1 | >98 | 80.1 | 19.9 |
| 15 | 10 | 20 | 4 | 1 | >98 | 69.7 | 30.3 |

Solvent = EtOH; Acid = $H_2SO_4$, 0.5 equiv.; Pressure 15 bar
*concentration of IV.1 in total amount of solvent

TABLE 2G

| No* | Temp [° C.] | Pressure [bar] | Dosing Time [h] | Post stirring time [h] | Conversion [%] | Pyrazole V.1 [area %] | NH-pyrazole $V^H.1$ [area %] |
|---|---|---|---|---|---|---|---|
| 16 | 10 | 15 | 4 | 1 | >98 | 80.1 | 19.9 |
| 17 | 10 | 15 | 10 | 1 | >98 | 90.6 | 9.3 |

Solvent = EtOH, Concentration of IV.1 in total amount of solvent = 15 wt.-%; Acid = $H_2SO_4$, 0.5 equiv.

TABLE 2H

| No* | Temp [° C.] | Acid [equiv] | Dosing Time [h] | Post stirring time [h] | Conversion [%] | Pyrazole V.1 [area %] | NH-pyrazole $V^H$.1 [area %] |
|---|---|---|---|---|---|---|---|
| 18 | 10 | 0.5 | 4 | 1 | >98 | 80.1 | 19.9 |
| 19 | 10 | 1 | 4 | 1 | >98 | 79.0 | 21.0 |

Solvent = EtOH, Concentration of IV.1 in total amount of solvent = 15 wt.-%; Acid = $H_2SO_4$, 0.5 equiv.; Pressure = 15 bar

The invention claimed is:

1. A process for preparing a pyrazole compound of formula V, or a salt, stereoisomer, tautomer or N-oxide thereof

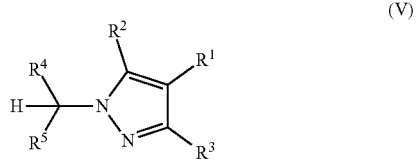

(V)

comprising the step of cyclizing a hydrazone substituted α,β-unsaturated carbonyl compound of formula IV

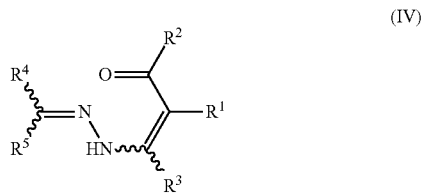

(IV)

by reacting it with hydrogen,
wherein the compound of formula IV is provided in a reaction mixture comprising as components:
(a) a hydrogenation catalyst;
(b) an acid selected from Brønsted acids, ammonium salts of Brønsted acids, and Lewis acids;
(c) a protic solvent; and optionally
(d) an aprotic solvent;
and wherein
$R^1$ is $C(O)OR^c$, wherein $R^c$ is $C_1$-$C_4$-alkyl or benzyl;
$R^2$ is $CH_3$, or fluoromethyl;
$R^3$ is H;
$R^4$ is selected from $C_1$-$C_4$-alkyl, which group is unsubstituted, or partially halogenated, and
$R^5$ is selected from $C_1$-$C_4$-alkyl.

2. The process of claim 1, wherein $R^2$ is $CH_3$; and $R^5$ is $CH_3$.

3. The process of claim 1, wherein $R^1$ is $C(O)OCH_2CH_3$; $R^2$ is $CH_3$; $R^4$ is $CH(CH_3)_2$; and $R^5$ is $CH_3$.

4. The process of claim 1, wherein the hydrogenation catalyst comprises palladium or platinum.

5. The process of claim 4, wherein the hydrogenation catalyst is Pt/C.

6. The process of claim 1, wherein the hydrogenation catalyst is present in the reaction mixture in an amount of at least 0.05 mol % based on the molar amount of the compound of formula IV.

7. The process of claim 1, wherein the acid is selected from the group consisting of $H_2SO_4$, methylsulfonic acid, trifluoroacetic acid, trichloroacetic acid, $H_3PO_4$, and $AlCl_3$.

8. The process of claim 1, wherein the protic solvent is selected from the group consisting of $C_1$-$C_4$-alkanols, $C_2$-$C_4$-alkandiols, water, acetic acid, formic acid, and mixtures thereof.

9. The process of claim 1, wherein the protic solvent is selected from the group consisting of methanol and ethanol, and mixtures thereof.

10. The process of claim 1, wherein the aprotic solvent is selected from the group consisting of aromatic solvents, alkane solvents, ether solvents, ester solvents, and mixtures thereof.

11. The process according of claim 1, wherein the compound of formula IV is present in the reaction mixture in an amount of at most 50 wt.-%, based on the total weight of the reaction mixture.

12. The process of claim 1, wherein the reaction with hydrogen is performed at a temperature of from 0° C. to 40° C.

13. The process of claim 1, wherein hydrogen is provided with a pressure of from 5 to 80 bar.

14. The process of claim 1, wherein a solution of compound of formula IV, wherein the solvent is selected from the group consisting of $C_1$-$C_4$-alkanols, $C_2$-$C_4$-alkandiols, water, acetic acid, formic acid, and mixtures thereof, is dosed to the reaction mixture comprising components a), b), c), and optionally d) wherein component a) is Pt/C, b) is $H_2SO_4$, c) is MeOH, and d) is, if present, toluene, MTBE, or EtOAc.

15. The process of claim 1, wherein the process further comprises the step of preparing the hydrazone substituted α,β-unsaturated carbonyl compound of formula IV

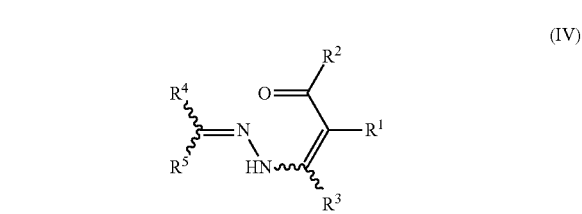

(IV)

by reacting an α,β-unsaturated carbonyl compound of formula III

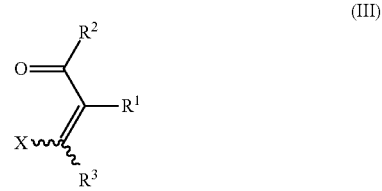

(III)

with a hydrazone compound of formula II

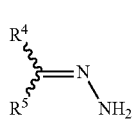
(II)

wherein
X is halogen, OH, $C_1$-$C_{10}$-alkoxy, $C_3$-$C_{10}$-cycloalkoxy, $C_1$-$C_{10}$-alkyl-S(O)$_2$O—, $C_1$-$C_{10}$-haloalkyl-S(O)$_2$O—, phenyl-S(O)$_2$O—, tolyl-S(O)$_2$O—, ($C_1$-$C_{10}$-alkyloxy)$_2$P(O)O—, $C_1$-$C_{10}$-cycloalkylthio, $C_1$-$C_{10}$-alkyl-C(O)S—, NH$_2$, $C_1$-$C_{10}$-alkylamino, $C_1$-$C_{10}$-dialkylamino, morpholino, N-methylpiperazino, or aza-$C_3$-$C_{10}$-cycloalkyl;
and $R^1$, $R^2$, $R^3$, $R^4$, and $R^5$ are defined as in claim 1.

16. The process of claim 15, wherein X is OCH$_2$CH$_3$.
17. The process of claim 15, wherein the step of preparing the pyrazole compound of formula V and the step of preparing the compound of formula IV are performed in a one-pot procedure, wherein the compound of formula IV is subjected to the cyclization reaction without previous purification.
18. The process of claim 15, wherein
(i) if the step of preparing the compound of formula IV is performed in a protic solvent or in a solvent mixture comprising a protic solvent and an aprotic solvent, the step of preparing the pyrazole compound of formula V is performed in the same solvent or solvent mixture as used in the step of preparing the compound of formula IV; or
(ii) if the step of preparing the compound of formula IV is performed in an aprotic solvent, the aprotic solvent is replaced by a protic solvent, or a protic solvent is added before the step of preparing the pyrazole compound of formula V.
19. A process for preparing a compound of formula VIII

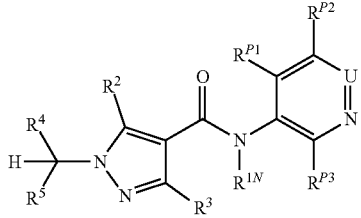
(VIII)

comprising the steps of:
cyclizing a hydrazone substituted α,β-unsaturated carbonyl compound of formula IV

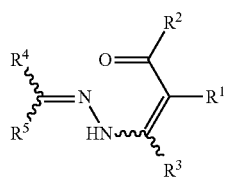
(IV)

by reacting it with hydrogen to form a compound of formula V

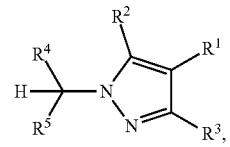
(V)

wherein the compound of formula IV is provided in a reaction mixture comprising as components:
(a) a hydrogenation catalyst;
(b) an acid selected from Bronsted acids, ammonium salts of Bronsted acids, and Lewis acids;
(c) a protic solvent; and optionally
(d) an aprotic solvent;
wherein
$R^1$ is C(O)OR$^c$ or CN, wherein Rc is $C_1$-$C_4$-alkyl or benzyl;
$R^2$ is CH$_3$, or fluoromethyl;
$R^3$ is H;
$R^4$ is selected from $C_1$-$C_4$-alkyl, which group is unsubstituted, or partially halogenated, and
$R^5$ is selected from $C_1$-$C_4$-alkyl; and
wherein the compound of formula V is a compound of formula Va or Vb

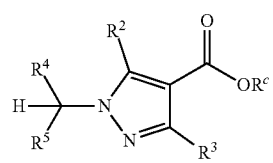
(Va)

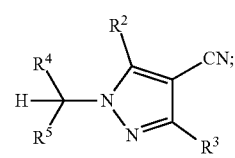
(Vb)

converting the compound of formula Va or Vb into a compound of formula Vc

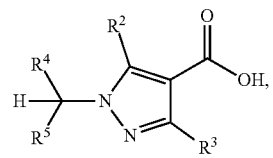
(Vc)

wherein
$R^2$ is CH$_3$, or fluoromethyl;
$R^3$ is H;
$R^4$ is selected from $C_1$-$C_4$-alkyl, which group is unsubstituted, or partially halogenated, and
$R^5$ is selected from $C_1$-$C_4$-alkyl;
converting the compound of formula Vc into a compound of formula VI

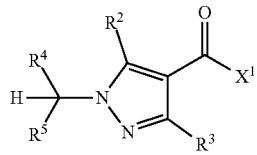

(VI)

wherein $X^1$ is leaving group selected from halogen, $N_3$, p-nitrophenoxy, and pentafluorophenoxy,
and wherein
$R^2$ is $CH_3$, or fluoromethyl;
$R^3$ is H;
$R^4$ is selected from $C_1$-$C_4$-alkyl, which group is unsubstituted, or partially halogenated, and
$R^5$ is selected from $C_1$-$C_4$-alkyl;
and,
converting the compound of formula VI into a compound of formula VIII

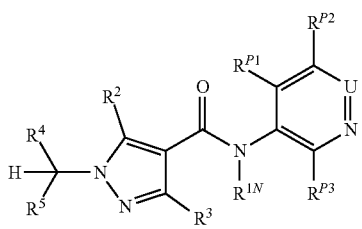

(VIII)

by reacting the compound of formula VI with a compound of formula VII

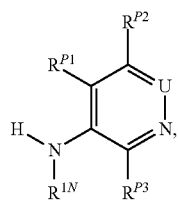

(VII)

wherein
$R^2$ is $CH_3$, or fluoromethyl;
$R^3$ is H;

$R^4$ is selected from $C_1$-$C_4$-alkyl, which group is unsubstituted, or partially halogenated, and $R^5$ is selected from $C_1$-$C_4$-alkyl; and wherein
U is N or CH;
$R^{P1}$, $R^{P2}$, and $R^{P3}$ are H; and
$R^{1N}$ is H, $C_1$-$C_2$-alkyl, or $C_1$-$C_2$alkoxy-$C_1$-$C_2$alkyl.

20. The process of claim 1, wherein a solution of compound of formula IV, wherein the solvent is selected from the group consisting of methanol and ethanol, and mixtures thereof, is dosed to the reaction mixture comprising components a), b), c), and optionally d) wherein component a) is Pt/C, b) is $H_2SO_4$, c) is MeOH, and d) is, if present, toluene, MTBE, or EtOAc.

21. The process of claim 1, wherein $R^1$ is $C(O)OR^c$.

22. A process for preparing a compound of formula VI

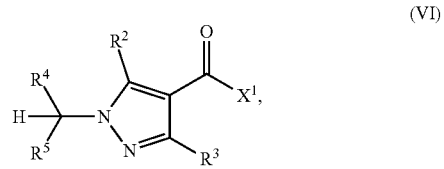

(VI)

the process comprising:
performing the process of claim 1 to provide the compound of formula V, wherein $R^1$, $R^2$, $R^3$, $R^4$, $R^5$, and $R^c$ are as defined in claim 1;
converting the compound of formula V into a compound of formula Vc

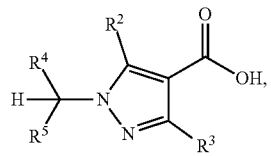

(Vc)

wherein $R^2$, $R^3$, $R^4$, and $R^5$ have the same meanings as above; and
converting the compound of formula Vc into the compound of formula VI above, wherein (i) $X^1$ is a leaving group selected from the group consisting of halogen, N3, p-nitrophenoxy, and pentafluorophenoxy, and (ii) $R^2$, $R^3$, $R^4$, and $R^5$ have the same meanings as above.

23. The process of claim 22, wherein $X^1$ is chlorine.

* * * * *